(12) United States Patent
Migot-Nabias et al.

(10) Patent No.: US 9,493,811 B2
(45) Date of Patent: Nov. 15, 2016

(54) METHOD OF NEONATAL SEROLOGICAL DIAGNOSIS

(75) Inventors: Florence Migot-Nabias, Eaubonne (FR); Celia Dechavanne, Paris (FR); Francois Guillonneau, Droue/Drouette (FR); Jean-Michel Dugoujon, Leguevin (FR); Marie-Paule Lefranc, Clapiers (FR)

(73) Assignees: INSTITUT DE RECHERCHE POUR LE DÉVELOPPEMENT (IRD), Marseille (FR); UNIVERSITE PARIS DESCARTES, Paris (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 8 days.

(21) Appl. No.: 14/238,107

(22) PCT Filed: Aug. 10, 2012

(86) PCT No.: PCT/EP2012/065737
§ 371 (c)(1),
(2), (4) Date: Feb. 10, 2014

(87) PCT Pub. No.: WO2013/021057
PCT Pub. Date: Feb. 14, 2013

(65) Prior Publication Data
US 2014/0178916 A1 Jun. 26, 2014

(30) Foreign Application Priority Data

Aug. 11, 2011 (FR) ...................... 11 57296

(51) Int. Cl.
*G01N 33/68* (2006.01)
*C12Q 1/37* (2006.01)

(52) U.S. Cl.
CPC ............. *C12Q 1/37* (2013.01); *G01N 33/6851* (2013.01); *G01N 33/6857* (2013.01); *G01N 2333/445* (2013.01); *G01N 2333/45* (2013.01)

(58) Field of Classification Search
None
See application file for complete search history.

(56) References Cited

U.S. PATENT DOCUMENTS

2010/0166749 A1 7/2010 Presta

OTHER PUBLICATIONS

Chen et al. (2007. Antibody analysis by ESI-TOF LC/Misapplication Note, Agilent Technologies Inc., 12 Pages.*
Akashi et al., Characterization of mouse switch variant antibodies by matrix-assisted laser desorption ionization mass spectrometry and electrospray ionization mass spectrometry. *J. Am. Soc. Mass Spec.*, 7(8): 707-21 (1996).
Goetze et al., Rapid LC-MS screening for IgG Fc modifications and allelic variants in blood. *Molec. Immunol.*, 49(1-2): 338-52 (2011).
Jefferis et al., Human immunoglobulin allotypes possible implications for immunogenicity. *MABS*, 1(4): 332-8 (2009).
Migot-Nabias et al., Imbalanced distribution of GM immunoglobulin allotypes according to the clinical presentation of plasmodium falciparum Malaria in Beninese children. *J. Infect. Dis.*, 198(12): 1892-5 (2008).
Oxelius, Preparation of IgG subclass allotypes from polyclonal IgG. *Scand. J. Immunol.*, 49(4): 395-8 (1999).
Search Report issued in connection with French Patent Application No. FR 1157296, dated Apr. 27, 2012.
International Search Report issued in connection with International Application No. PCT/EP2012/065737, European Patent Office, dated Apr. 23, 2013.

* cited by examiner

*Primary Examiner* — Padma V Baskar
(74) *Attorney, Agent, or Firm* — Marshall, Gerstein & Borun LLP

(57) ABSTRACT

The present invention provides a method for determining the amino acid polymorphisms of heavy gamma chain of immunoglobulins G by a proteomic approach. This method distinguishes the immunoglobulins of the mother and those of the newborn in a blood sample obtained during the first months of the child's life. The invention also relates to the use of this method in the early diagnosis of vertically transmitted diseases in the neonate. The invention also provides peptides distinctive of G3m and IGHG3 alleles, and a kit comprising said peptides.

6 Claims, 6 Drawing Sheets

| Proteotypic Peptides* | A** | MALDI m/z | MALDI m/z (Mox) | ESI-TRAP m/z | ESI-TRAP m/z (Mox) |
|---|---|---|---|---|---|
| CH2 Domain | | | | | |
| K . TKPWEEQYNSTFR . V | 0 | 1685.8 | | 843.4 / 562.6 | |
| K . TKPREEQYNSTFR . V | 1 | 1655.8 | | 828.4 / 547.8 / 414.7 | |
| K . LREEQYNSTFR . V | 1 | 1442.7 | | 721.9 / 481.6 | |
| V . DGVEVHNAKTKPWEEQYNSTFR . V | 1 | 2635.3 | | 1318.1 / 879.1 / 879.1 / 659.6 | |
| R . EEQYNSTFRVVSVLTVLHQ . D | 1 | 2249.2 | | 1125.1 / 750.4 / 563.0 | |
| R . EEQYNSTFRVVSVLTVVHQ . D | 1 | 2235.1 | | 1118.1 / 745.7 / 559.5 | |
| K . TKPWEEQYNSTFRVVSVLTVLHQ . D | 1 | 2761.4 | | 1381.2 / 921.1 / 691.1 | |
| CH3 Domain | | | | | |
| K . GFYPSDIAVEWESSGQPENNYK . T | 1 | 2517.1 | 2565.1 | 1259.1 / 839.7 / 630.0 | |
| K . GFYPSDIAMEWESSGQPENNYK . T | 1 | 2549.1 | | 1275.0 / 850.4 / 638.0 | 1283.0 / 855.7 / 642.0 |
| K . GFYPSDIAVEWESSGQPENNYNTTPPML . D | 1 | 3143.4 | 3159.4 | 1572.2 / 1048v5 / 786.6 | 1580.2 / 1053.8 / 790.6 |
| K . GFYPSDIAVEWESSGQPNNNYNTTPPML . D | 1 | 3128.4 | 3144.4 | 1564.7 / 1043.5 / 782.8 | 1572.7 / 1048.8 / 786.8 |
| K . GFYPSDIAVEWESSGQPENNYNTTPPVL . D | 1 | 3111.4 | | 1556.2 / 1037.8 / 778.6 | |
| K . GFYPSDIAVEWESNGQPENNYNTTPPML . D | 1 | 3170.4 | 31986.4 | 1585.7 / 1057.5 / 793.4 | 1593.7 / 1062.8 / 797.4 |
| S . DIAVEWESSGQPENNYK . T | 0 | 1965.9 | 1981.9 | 983.4 / 656.0 / 492.2 | 991.4 / 661.3 / 496.2 |
| S . DIAMEWESSGQPENNYK . T | 0 | 1997.9 | 2013.9 | 999.4 / 666.6 / 500.2 | 1007.4 / 672.0 / 504.2 |
| S . DIAVEWESSGQPENNYNTTPPML . D | 0 | 2592.2 | 2608.2 | 1296.6 / 864.7 / 648.8 | 1304.6 / 870.1 / 652.8 |

Figure 2(A)

| Proteotypic Peptides* | A** | MALDI m/z | MALDI m/z (Mox) | ESI-TRAP m/z | ESI-TRAP m/z (Mox) |
|---|---|---|---|---|---|
| S . DIAVEWESSGQPNNNYNTTPPML . D | 0 | 2577.2 | 2593.2 | 1289.1 / 859.7 / 645.0 | 1297.1 / 865.1 / 649.0 |
| S . DIAVEWESSGQPENNYNTTPPVL . D | 0 | 2560.2 | | - | - |
| S . DIAVEWESNGQPENNYNTTPPML . D | 0 | 2619.2 | 2635.2 | 1280.6 / 854.1 / 640.8 | - |
| K . SRWQQGNIFSC^CSVMHEALHNHYTQK . S | 1 | 3058.4 | 3074.4 | 1310.1 / 873.7 / 655.5 | 1318.1 / 879.1 / 659.5 |
| K . SRWQQGNIFSC^CSVMHEALHNR . F | 1 | 2557.2 | 2573.2 | 1529.7 / 1020.1 / 765.4 | 1537.7 / 1025.5 / 769.4 |
| K . SRWQEGNVFSC^CSVMHEALHNR . F | 1 | 2544.2 | 2560.2 | 1279.1 / 853.1 / 640.0 | 1287.1 / 858.4 / 644.0 |
| K . SRWQEGNIFSC^CSVMHEALHNR . F | 1 | 2558.2 | 2574.2 | 1272.6 / 848.7 / 636.8 | 1280.6 / 854.1 / 640.8 |
| R . WQQGNIFSC^CSVMHEALHNHYTQK . S | 0 | 2815.3 | 2831.3 | 1279.6 / 853.4 / 640.3 | 1287.6 / 858.7 / 644.3 |
| R . WQQGNIFSC^CSVMHEALHNR . F | 0 | 2314.1 | 2330.1 | 1408.1 / 939.1 / 704.6 | 1416.1 / 944.4 / 708.6 |
| R . WQEGNVFSC^CSVMHEALHNR . F | 0 | 2301.0 | 2317.0 | 1157.5 / 772.0 / 579.3 | 1165.5 / 777.4 / 583.3 |
| R . WQEGNIFSC^CSVMHEALHNR . F | 0 | 2315.0 | 2331.0 | 1151.0 / 767.7 / 576.0 | 1159.0 / 773.0 / 580.0 |
| R . WQEGNIFSC^CSVMHEALHNR . F | 0 | 2315.0 | 2331.0 | 1158.0 / 772.3 / 579.5 | 1166.0 / 777.7 / 583.5 |
| R . WQQGNIFSC^CSVMHEALHNHYTQKSLSLSPGK . S | 1 | 3584.7 | 3600.7 | 1792.9 / 1195.6 / 896.9 | 1800.9 / 1200.9 / 900.9 |
| R . WQQGNIFSC^CSVMHEALHNRFTQK . S | 1 | 2818.3 | 2834.3 | 1409.7 / 940.1 / 705.3 | 1417.7 / 945.4 / 709.3 |
| R . WQEGNVFSC^CSVMHEALHNRFTQK . S | 1 | 2805.3 | 2821.3 | 1403.1 / 935.8 / 702.1 | 1411.1 / 941.1 / 706.1 |
| R . WQEGNIFSC^CSVMHEALHNRFTQK . S | 1 | 2819.3 | 2835.3 | 1410.2 / 940.4 / 705.6 | 1418.2 / 945.8 / 709.6 |
| R . WQQGNIFSC^CSVMHEALHNRYTQK . S | 1 | 2834.3 | 2850.3 | 1417.7 / 945.4 / 709.3 | 1425.7 / 950.8 / 713.3 |

Figure 2(B)

A. ORBI-TRAP
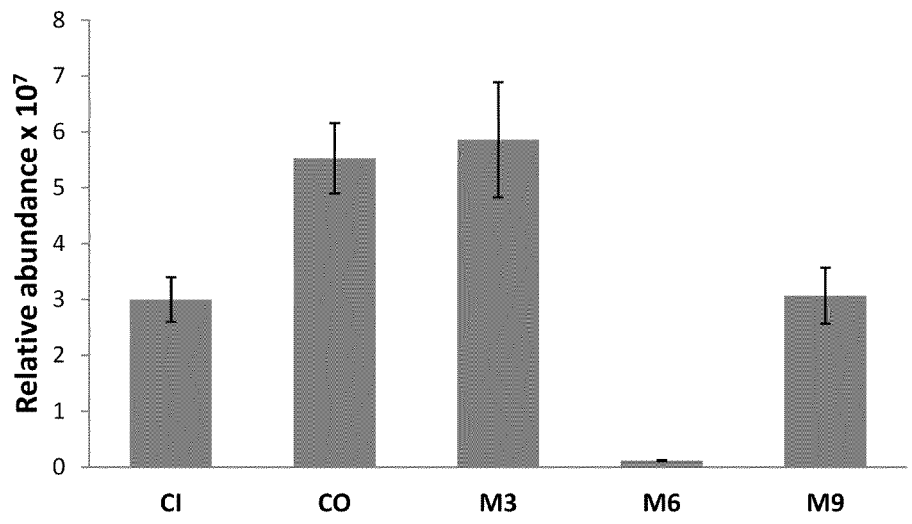
B. SRM
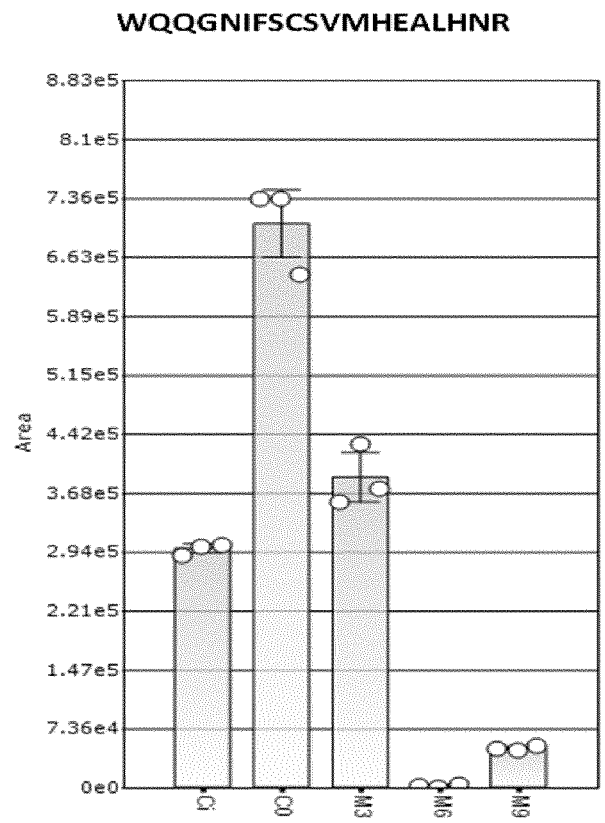
Figure 5

SEQUENCE LISTING

```
<160> NUMBER OF SEQ ID NOS: 32

<210> SEQ ID NO 1
<211> LENGTH: 13
<212> TYPE: PRT
<213> ORGANISM: Homo sapiens

<400> SEQUENCE: 1

Thr Lys Pro Trp Glu Glu Gln Tyr Asn Ser Thr Phe Arg
1               5                   10

<210> SEQ ID NO 2
<211> LENGTH: 13
<212> TYPE: PRT
<213> ORGANISM: Homo sapiens

<400> SEQUENCE: 2

Thr Lys Pro Arg Glu Glu Gln Tyr Asn Ser Thr Phe Arg
1               5                   10

<210> SEQ ID NO 3
<211> LENGTH: 11
<212> TYPE: PRT
```

```
<213> ORGANISM: Homo sapiens

<400> SEQUENCE: 3

Leu Arg Glu Glu Gln Tyr Asn Ser Thr Phe Arg
1               5                   10

<210> SEQ ID NO 4
<211> LENGTH: 22
<212> TYPE: PRT
<213> ORGANISM: Homo sapiens

<400> SEQUENCE: 4

Asp Gly Val Glu Val His Asn Ala Lys Thr Lys Pro Trp Glu Gln
1               5                   10                  15

Tyr Asn Ser Thr Phe Arg
            20

<210> SEQ ID NO 5
<211> LENGTH: 19
<212> TYPE: PRT
<213> ORGANISM: Homo sapiens

<400> SEQUENCE: 5

Glu Glu Gln Tyr Asn Ser Thr Phe Arg Val Val Ser Val Leu Thr Val
1               5                   10                  15

Leu His Gln

<210> SEQ ID NO 6
<211> LENGTH: 19
<212> TYPE: PRT
<213> ORGANISM: Homo sapiens

<400> SEQUENCE: 6

Glu Glu Gln Tyr Asn Ser Thr Phe Arg Val Val Ser Val Leu Thr Val
1               5                   10                  15

Val His Gln

<210> SEQ ID NO 7
<211> LENGTH: 23
<212> TYPE: PRT
<213> ORGANISM: Homo sapiens

<400> SEQUENCE: 7

Thr Lys Pro Trp Glu Glu Gln Tyr Asn Ser Thr Phe Arg Val Val Ser
1               5                   10                  15

Val Leu Thr Val Leu His Gln
            20

<210> SEQ ID NO 8
<211> LENGTH: 22
<212> TYPE: PRT
<213> ORGANISM: Homo sapiens

<400> SEQUENCE: 8

Gly Phe Tyr Pro Ser Asp Ile Ala Val Glu Trp Glu Ser Ser Gly Gln
1               5                   10                  15

Pro Glu Asn Asn Tyr Lys
            20

<210> SEQ ID NO 9
<211> LENGTH: 22
<212> TYPE: PRT
```

<213> ORGANISM: Homo sapiens

<400> SEQUENCE: 9

Gly Phe Tyr Pro Ser Asp Ile Ala Met Glu Trp Glu Ser Ser Gly Gln
1               5                   10                  15

Pro Glu Asn Asn Tyr Lys
            20

<210> SEQ ID NO 10
<211> LENGTH: 28
<212> TYPE: PRT
<213> ORGANISM: Homo sapiens

<400> SEQUENCE: 10

Gly Phe Tyr Pro Ser Asp Ile Ala Val Glu Trp Glu Ser Ser Gly Gln
1               5                   10                  15

Pro Glu Asn Asn Tyr Asn Thr Thr Pro Pro Met Leu
            20                  25

<210> SEQ ID NO 11
<211> LENGTH: 28
<212> TYPE: PRT
<213> ORGANISM: Homo sapiens

<400> SEQUENCE: 11

Gly Phe Tyr Pro Ser Asp Ile Ala Val Glu Trp Glu Ser Ser Gly Gln
1               5                   10                  15

Pro Asn Asn Asn Tyr Asn Thr Thr Pro Pro Met Leu
            20                  25

<210> SEQ ID NO 12
<211> LENGTH: 28
<212> TYPE: PRT
<213> ORGANISM: Homo sapiens

<400> SEQUENCE: 12

Gly Phe Tyr Pro Ser Asp Ile Ala Val Glu Trp Glu Ser Ser Gly Gln
1               5                   10                  15

Pro Glu Asn Asn Tyr Asn Thr Thr Pro Pro Val Leu
            20                  25

<210> SEQ ID NO 13
<211> LENGTH: 28
<212> TYPE: PRT
<213> ORGANISM: Homo sapiens

<400> SEQUENCE: 13

Gly Phe Tyr Pro Ser Asp Ile Ala Val Glu Trp Glu Ser Asn Gly Gln
1               5                   10                  15

Pro Glu Asn Asn Tyr Asn Thr Thr Pro Pro Met Leu
            20                  25

<210> SEQ ID NO 14
<211> LENGTH: 17
<212> TYPE: PRT
<213> ORGANISM: Homo sapiens

<400> SEQUENCE: 14

Asp Ile Ala Val Glu Trp Glu Ser Ser Gly Gln Pro Glu Asn Asn Tyr
1               5                   10                  15

Lys

```
<210> SEQ ID NO 15
<211> LENGTH: 17
<212> TYPE: PRT
<213> ORGANISM: Homo sapiens

<400> SEQUENCE: 15

Asp Ile Ala Met Glu Trp Glu Ser Ser Gly Gln Pro Glu Asn Asn Tyr
1               5                   10                  15

Lys

<210> SEQ ID NO 16
<211> LENGTH: 23
<212> TYPE: PRT
<213> ORGANISM: Homo sapiens

<400> SEQUENCE: 16

Asp Ile Ala Val Glu Trp Glu Ser Ser Gly Gln Pro Glu Asn Asn Tyr
1               5                   10                  15

Asn Thr Thr Pro Pro Met Leu
            20

<210> SEQ ID NO 17
<211> LENGTH: 23
<212> TYPE: PRT
<213> ORGANISM: Homo sapiens

<400> SEQUENCE: 17

Asp Ile Ala Val Glu Trp Glu Ser Ser Gly Gln Pro Asn Asn Asn Tyr
1               5                   10                  15

Asn Thr Thr Pro Pro Met Leu
            20

<210> SEQ ID NO 18
<211> LENGTH: 23
<212> TYPE: PRT
<213> ORGANISM: Homo sapiens

<400> SEQUENCE: 18

Asp Ile Ala Val Glu Trp Glu Ser Ser Gly Gln Pro Glu Asn Asn Tyr
1               5                   10                  15

Asn Thr Thr Pro Pro Val Leu
            20

<210> SEQ ID NO 19
<211> LENGTH: 23
<212> TYPE: PRT
<213> ORGANISM: Homo sapiens

<400> SEQUENCE: 19

Asp Ile Ala Val Glu Trp Glu Ser Asn Gly Gln Pro Glu Asn Asn Tyr
1               5                   10                  15

Asn Thr Thr Pro Pro Met Leu
            20

<210> SEQ ID NO 20
<211> LENGTH: 25
<212> TYPE: PRT
<213> ORGANISM: Homo sapiens
<220> FEATURE:
<221> NAME/KEY: MISC_FEATURE
<223> OTHER INFORMATION: Cys is a carbamidomethylated Cys

<400> SEQUENCE: 20
```

```
Ser Arg Trp Gln Gln Gly Asn Ile Phe Ser Cys Ser Val Met His Glu
1               5                   10                  15

Ala Leu His Asn His Tyr Thr Gln Lys
            20                  25

<210> SEQ ID NO 21
<211> LENGTH: 21
<212> TYPE: PRT
<213> ORGANISM: Homo sapiens
<220> FEATURE:
<221> NAME/KEY: MISC_FEATURE
<223> OTHER INFORMATION: Cys is a carbamidomethylated Cys

<400> SEQUENCE: 21

Ser Arg Trp Gln Gln Gly Asn Ile Phe Ser Cys Ser Val Met His Glu
1               5                   10                  15

Ala Leu His Asn Arg
            20

<210> SEQ ID NO 22
<211> LENGTH: 21
<212> TYPE: PRT
<213> ORGANISM: Homo sapiens
<220> FEATURE:
<221> NAME/KEY: MISC_FEATURE
<223> OTHER INFORMATION: Cys is a carbamidomethylated Cys

<400> SEQUENCE: 22

Ser Arg Trp Gln Glu Gly Asn Val Phe Ser Cys Ser Val Met His Glu
1               5                   10                  15

Ala Leu His Asn Arg
            20

<210> SEQ ID NO 23
<211> LENGTH: 21
<212> TYPE: PRT
<213> ORGANISM: Homo sapiens
<220> FEATURE:
<221> NAME/KEY: MISC_FEATURE
<223> OTHER INFORMATION: Cys is a carbamidomethylated Cys

<400> SEQUENCE: 23

Ser Arg Trp Gln Glu Gly Asn Ile Phe Ser Cys Ser Val Met His Glu
1               5                   10                  15

Ala Leu His Asn Arg
            20

<210> SEQ ID NO 24
<211> LENGTH: 23
<212> TYPE: PRT
<213> ORGANISM: Homo sapiens
<220> FEATURE:
<221> NAME/KEY: MISC_FEATURE
<223> OTHER INFORMATION: Cys is a carbamidomethylated Cys

<400> SEQUENCE: 24

Trp Gln Gln Gly Asn Ile Phe Ser Cys Ser Val Met His Glu Ala Leu
1               5                   10                  15

His Asn His Tyr Thr Gln Lys
            20

<210> SEQ ID NO 25
<211> LENGTH: 19
<212> TYPE: PRT
```

-continued

```
<213> ORGANISM: Homo sapiens
<220> FEATURE:
<221> NAME/KEY: MISC_FEATURE
<223> OTHER INFORMATION: Cys is a carbamidomethylated Cys

<400> SEQUENCE: 25

Trp Gln Gln Gly Asn Ile Phe Ser Cys Ser Val Met His Glu Ala Leu
1               5                   10                  15

His Asn Arg

<210> SEQ ID NO 26
<211> LENGTH: 19
<212> TYPE: PRT
<213> ORGANISM: Homo sapiens
<220> FEATURE:
<221> NAME/KEY: MISC_FEATURE
<223> OTHER INFORMATION: Cys is a carbamidomethylated Cys

<400> SEQUENCE: 26

Trp Gln Glu Gly Asn Val Phe Ser Cys Ser Val Met His Glu Ala Leu
1               5                   10                  15

His Asn Arg

<210> SEQ ID NO 27
<211> LENGTH: 19
<212> TYPE: PRT
<213> ORGANISM: Homo sapiens
<220> FEATURE:
<221> NAME/KEY: MISC_FEATURE
<223> OTHER INFORMATION: Cys is a carbamidomethylated Cys

<400> SEQUENCE: 27

Trp Gln Glu Gly Asn Ile Phe Ser Cys Ser Val Met His Glu Ala Leu
1               5                   10                  15

His Asn Arg

<210> SEQ ID NO 28
<211> LENGTH: 31
<212> TYPE: PRT
<213> ORGANISM: Homo sapiens
<220> FEATURE:
<221> NAME/KEY: MISC_FEATURE
<223> OTHER INFORMATION: Cys is a carbamidomethylated Cys

<400> SEQUENCE: 28

Trp Gln Gln Gly Asn Ile Phe Ser Cys Ser Val Met His Glu Ala Leu
1               5                   10                  15

His Asn His Tyr Thr Gln Lys Ser Leu Ser Leu Ser Pro Gly Lys
            20                  25                  30

<210> SEQ ID NO 29
<211> LENGTH: 23
<212> TYPE: PRT
<213> ORGANISM: Homo sapiens
<220> FEATURE:
<221> NAME/KEY: MISC_FEATURE
<223> OTHER INFORMATION: Cys is a carbamidomethylated Cys

<400> SEQUENCE: 29

Trp Gln Gln Gly Asn Ile Phe Ser Cys Ser Val Met His Glu Ala Leu
1               5                   10                  15

His Asn Arg Phe Thr Gln Lys
            20
```

```
<210> SEQ ID NO 30
<211> LENGTH: 23
<212> TYPE: PRT
<213> ORGANISM: Homo sapiens
<220> FEATURE:
<221> NAME/KEY: MISC_FEATURE
<223> OTHER INFORMATION: Cys is a carbamidometylated Cys

<400> SEQUENCE: 30

Trp Gln Glu Gly Asn Val Phe Ser Cys Ser Val Met His Glu Ala Leu
1               5                   10                  15

His Asn Arg Phe Thr Gln Lys
            20

<210> SEQ ID NO 31
<211> LENGTH: 23
<212> TYPE: PRT
<213> ORGANISM: Homo sapiens
<220> FEATURE:
<221> NAME/KEY: MISC_FEATURE
<223> OTHER INFORMATION: Cys is a carbamidomethylated Cys

<400> SEQUENCE: 31

Trp Gln Glu Gly Asn Ile Phe Ser Cys Ser Val Met His Glu Ala Leu
1               5                   10                  15

His Asn Arg Phe Thr Gln Lys
            20

<210> SEQ ID NO 32
<211> LENGTH: 23
<212> TYPE: PRT
<213> ORGANISM: Homo sapiens
<220> FEATURE:
<221> NAME/KEY: MISC_FEATURE
<223> OTHER INFORMATION: Cys is a carbamidomethylated Cys

<400> SEQUENCE: 32

Trp Gln Gln Gly Asn Ile Phe Ser Cys Ser Val Met His Glu Ala Leu
1               5                   10                  15

His Asn Arg Tyr Thr Gln Lys
            20
```

METHOD OF NEONATAL SEROLOGICAL DIAGNOSIS

RELATED APPLICATION

The present application claims priority to French Patent Application No. FR 11 57296 filed on Aug. 11, 2011. The French patent application is incorporated herein by reference in its entirety.

FIELD OF THE INVENTION

The present invention relates to a method for detecting amino acid polymorphisms of immunoglobulin heavy chains. The method allows in particular the determination of the allotypes of immunoglobulins in a blood sample, in particular making possible to identify and quantify immunoglobulins from the mother and from the newborn. The invention also relates to the use of this method as a serological diagnostic tool in the area of vertically transmitted diseases.

BACKGROUND OF THE INVENTION

The biological diagnosis of certain vertically transmitted diseases in the newborn is particularly difficult when the available methods of antigen detection are not reliable. Indeed, serological tests cannot be carried out in infants due to the presence, up to the age of 6 months, of maternal antibodies transmitted during pregnancy (Simister et al., J. Reprod. Immun., 1997, 37: 1-23; Williams et al., Arch. Dis. Childhood, 1969, 44: 511-514), which prevents assessment of the proportion of antibodies generated by the child. Preemptive treatments, which are not devoid of toxicity or of undesirable effects, are therefore administered, from birth, to a newborn suspected of a congenital disease. These treatments are maintained until the child is at least 6 months old and/or until it is possible to carry out a serological examination allowing assay of only the child's antibodies, once the antibodies transmitted from the mother have been completely eliminated.

This is, for example, the case of Chagas disease, also known as South American trypanosomiasis, a parasitic infection caused by *Trypanosoma cruzi*, which is rife in the tropical regions of South America and Central America. In some neonates, congenital Chagas disease can be diagnosed by microscopic examination of the parasite in a blood sample and/or by amplification of portions of parasitic genes by PCR (Schijman et al., J. Antimicrob. Chemother., 2003, 52: 441-449). However, these techniques are limited by obstacles that prevent from reaching a definitive diagnostic conclusion. These obstacles are notably linked to thresholds that are too high for the sensitivity of microscopic detection, presenting a risk of a false-negative diagnosis, and to PCR amplification of DNA derived from fragments of soluble parasitic genetic material that have crossed the placental barrier (rather than from viable parasites), presenting a risk of a false-positive diagnosis. It is therefore necessary to carry out a serological test 6 to 9 months after birth to rule out the presence of any undetected infection (Chippaux et al., Tropical Med. International Health, 2010, 15: 87-93). Due to the limitations of the available diagnostic techniques, treatment based on benznidazole is administered preemptively to the newborn immediately after birth. Although early administration favors both efficacy and tolerability of benznidazole, this substance is toxic, induces many side-effects, and cannot be administered without follow-up medical supervision. Moreover, such a treatment represents a considerable cost for the families affected by this disease, occurring in countries with low economic strength.

A similar problem is encountered in the case of toxoplasmosis, a parasitic infection caused by the protozoan *Toxoplasma gondii*. Although infection by this parasite occurs in all regions of the world, it is more prevalent in certain parts of Europe, the Caribbean and South America than in Asia, the United States or Australia. Congenital infection can be diagnosed by PCR, and a Western blot qualitative test is used for comparing the immunological profiles of the IgM and IgG from the mother and the child, without determining the amounts of immunoglobulins (Pinon et al., J. Clin. Microbiol., 2001, 39: 2267-2271). However, this test requires maternal plasma to be collected shortly after birth, and its use is therefore exclusively perinatal. Conversely, measurement by enzyme immunoassay (EIA) of the differences between the avidity of the antibodies of the mother and those of the child can only be performed about 6 months after birth. To overcome these shortcomings, effective but aggressive treatment with pyrimethamine and sulphonamides is administered to the newborn preemptively. However, without close medical supervision this treatment can have dramatic side-effects.

Malaria is another example of parasitic disease for which understanding of the mechanisms of acquisition of specific natural immunity by the infant might be of help for proposing public health measures for protecting groups at risk and for better targeting future strategies of antimalarial vaccination. Malaria is due to a parasite of the genus *Plasmodium*, of which the species *Plasmodium falciparum* is the most common and the most pathogenic in humans and that which is responsible for fatal cases. Malaria affects about a hundred countries in the world, particularly in the underprivileged tropical zones of Africa, Asia and Latin America. It mainly affects children under 5 years of age and pregnant women, who are particularly vulnerable because the placenta constitutes a target where the parasites may accumulate. In a pregnant woman, malarial infection can cause a whole range of detrimental effects: spontaneous abortion, premature birth, low birth weight, congenital transmission, and neonatal death.

In all these cases of vertically transmitted infectious diseases, it therefore seems to be crucial to develop new strategies for accurate and definitive diagnosis of a congenital disease in the first months of life of the newborn. An early biological diagnosis of these infections could provide valuable assistance in the decision of whether to initiate or curtail drug treatments, with a benefit in terms of children's health, but also to combat these diseases and their consequences.

SUMMARY OF THE INVENTION

The present invention relates generally to a method for distinguishing between the immunoglobulins of the mother and of the neonate in a blood sample taken during the first months of the child's life. This method is, in particular, applicable to the diagnosis of vertically transmitted diseases. More specifically, the inventors have shown that it is possible to use the allotype polymorphisms of immunoglobulins or other polymorphic amino acids of the heavy chains of immunoglobulins for separately identifying and quantifying the immunoglobulins of the mother and of the newborn. They have developed a technique for differentially detecting and quantifying, in the neonate's plasma, the immunoglobulins G (IgG) of the mother and those of the child. This technique is based on a proteomic approach and makes use of the individual characteristics of IgG3s, the most polymorphic IgG subclass. The inventors have identified, among the peptides obtained by a series of enzymatic digestions performed on the Fc fragment of purified IgG3s, a list of peptides indicative of the identity of G3m and IGHG3 alleles. The method developed was validated on blood samples from a Beninese mother and her baby and the results were confirmed by previous determination of the polymorphism of the IgG allotypes using an immunohaematologic technique allowing definition of the G3m alleles of the child from determinations performed on the child and on his biological parents (see Examples).

Consequently, in a first aspect, the present invention provides an in vitro method for detecting antibodies in a newborn, the method comprising steps of: determining, by mass spectrometry, the G3m and IGHG3 alleles present in a blood sample obtained from the newborn, the blood sample comprising IgG3s of the newborn and maternal IgG3s transmitted to the newborn during pregnancy; comparing the G3m and IGHG3 alleles of the IgG3s present in the blood sample obtained from the newborn to the G3m and IGHG3 alleles of the IgG3s present in a blood sample obtained from the newborn's mother; and detecting, and optionally quantifying, the IgG3s of the newborn.

In the methods of the invention relative to newborns, the blood sample obtained from the newborn is obtained between the birth and the 9$^{th}$ month of the newborn's life. In certain embodiments, the blood sample obtained from the newborn is a plasma sample.

Preferably, a method according to the invention further comprises steps of: isolating the IgG3s present in the blood sample obtained from the newborn; submitting the isolated IgG3s to an enzymatic digestion in order to obtain a mixture of proteotypic peptides of IgG3; and detecting, by mass spectrometry, the presence of at least one peptide distinctive of G3m and/or IGHG3 alleles in order to determine the alleles of the IgG3s present in the blood sample obtained from the newborn.

The step of isolating the IgG3s present in the blood sample from the newborn may be performed using any appropriate method. In certain embodiments, the IgG3s are isolated by affinity chromatography (for example using a Protein A column and/or a Protein G column). In other embodiments, the IgG3s are isolated by liquid chromatography, in particular by Fast Protein Liquid Chromatography (FPLC).

The step of submitting the isolated IgG3s to a proteolysis or an enzymatic digestion may be performed using any appropriate method leading to a mixture of proteotypic peptides of IgG3.

For example, in certain embodiments, the enzymatic digestion comprises a digestion in the presence of the endoproteinase AspN followed by a digestion in the presence of trypsin, or alternatively a digestion in the presence of both AspN and trypsin. In such embodiments, the at least one peptide distinctive of G3m and/or IGHG3 alleles, allowing determination of the alleles of the IgG3s present in the blood sample obtained from the newborn, is selected from the group consisting of the peptides of SEQ ID NOs: 1 to 32 and any combination thereof.

In certain embodiments, the mass spectrometry analysis performed in a method according to the invention is carried out using a tandem mass spectrometry technique, such as MALDI-TOF/TOF, ESI-LTQ-Orbitrap or SRM MS/MS.

The alleles of the IgG3s present in the blood sample of the newborn's mother may be determined using any appropriate method. In certain embodiments, the allotypes of the IgG3s present in the blood sample of the mother are determined using an immunohaematologic technique, preferably a technique of haemagglutination inhibition. In other embodiments, the alleles of the IgG3s present in the blood sample of the mother are determined using a method according to the invention.

The methods described herein which allow the specific identification and quantification of the immunoglobulins of the mother and those of the newborn, find application in the field of diagnosis of vertically transmitted diseases, such as viral, bacterial and parasitic infectious diseases.

Consequently, in another aspect, the present invention provides an in vitro method for diagnosing, in a newborn, an infectious disease caused by a pathogen, the method comprising steps of: determining, by mass spectrometry, the alleles of the pathogen-specific IgG3s present in a blood sample obtained from the newborn, the blood sample comprising pathogen-specific IgG3s of the newborn and pathogen-specific IgG3s of maternal origin transmitted to the newborn during pregnancy; comparing the alleles of the pathogen-specific IgG3s present in the blood sample of the newborn to the alleles of the IgG3s present in a blood sample obtained from the newborn's mother; and detecting, and optionally quantifying, the pathogen-specific IgG3s of the newborn.

In the diagnostic methods according to the invention, the blood sample obtained from the newborn is obtained between the birth and the 9$^{th}$ month of the newborn's life. In certain embodiments, the blood sample obtained from the newborn is a plasma sample.

Preferably, a diagnostic method according to the invention further comprises: isolating the pathogen-specific IgG3s present in the blood sample obtained from the newborn; submitting the isolated pathogen-specific IgG3s to an enzymatic digestion in order to obtain a mixture of proteotypic peptides of IgG3; and detecting, by mass spectrometry, among the mixture of proteotypic peptides of IgG3, the presence of at least one peptide distinctive of G3m and/or IGHG3 alleles in order to determine the alleles of the pathogen-specific IgG3s present in the blood sample obtained from the newborn.

In certain preferred embodiments, the at least one peptide distinctive of G3m and/or IGHG3 alleles, allowing determination of the alleles of the pathogen-specific IgG3s present in the blood sample obtained from the newborn, is selected from the group consisting of the peptides of SEQ ID NOs: 1 to 32 and any combination thereof. In such embodiments, the enzymatic digestion of the pathogen-specific IgG3s is carried out in the presence of AspN and trypsin.

In certain embodiments, the infectious disease diagnosed by a method according to the invention is a viral infectious disease, and the isolated IgG3s are specific of the virus responsible for the infectious disease.

In other embodiments, the infectious disease diagnosed by a method according to the invention is a bacterial infectious disease, and the isolated IgG3s are specific of the bacteria responsible for the infectious disease.

In yet other embodiments, the infectious disease diagnosed by a method according to the invention is a parasitic infectious disease, and the isolated IgG3s are specific of the parasite responsible for the infectious disease. For example, when the parasitic infectious disease is malaria, the isolated IgG3s are specific of the parasite *Plasmodium falciparum*; when the parasitic infectious disease is Chagas disease, the isolated IgG3s are specific of the parasite *Trypanosoma* cruzi; and when the parasitic infectious disease is toxoplasmosis, the isolated IgG3s are specific of the parasite *Toxoplasma gondii*.

In a diagnostic method according to the invention, the step of isolating the pathogen-specific IgG3s present in the blood sample from the newborn may be performed using any suitable method. In certain embodiments, total IgG3s are first isolated from the blood sample, for example by affinity chromatography out by FPLC; and then the pathogen-specific IgG3s are isolated from the total IgG3s. Isolating the pathogen-specific IgG3s from the total IgG3s may be performed using any appropriate technique, for example via formation of an immunocomplex resulting from contact between the total IgG3s with a pathogen-specific antigenic preparation.

The other steps in a diagnostic method according to the invention may be carried out like when total IgG3s are used instead of pathogen-specific IgG3s.

The alleles of the IgG3s present in the blood sample obtained from the newborn's mother may be determined using any appropriate method on the total IgG3s or on the pathogen-specific IgG3s. In certain embodiments, the determination is carried out using an immunohaematologic technique, preferably a technique of haemagglutination inhibition. In other embodiments, the determination is carried out using a method according to the invention. Indeed, as will be recognized by one skilled in the art, a method according to the invention may be used to determine the polymorphism of the IgG alleles of an individual at any stage of his or her life, i.e., aside from any consideration of the problems connected with the diagnosis of vertically transmitted diseases in newborns.

Consequently, in another aspect, the present invention provides a method for determining the alleles of IgG3s of an individual, the method comprising a step of: determining, by mass spectrometry, the amino acid polymorphism of the heavy gamma chains of IgG3s present in a blood sample obtained from the individual.

In certain embodiments, this method further comprises steps of: isolating the IgG3s present in the blood sample from the individual; submitting the isolated IgG3s to an enzymatic digestion in order to obtain a mixture of proteotypic peptides of IgG3; and detecting, by mass spectrometry, among the mixture of proteotypic peptides of IgG3, the presence of at least one peptide distinctive of G3m and/or IGHG3 alleles in order to determine the amino acid polymorphism of the heavy gamma chains of IgG3s present in the blood sample from the individual.

Preferably, the enzymatic digestion comprises a digestion in the presence of the endoproteinase AspN followed by a digestion in the presence of trypsin, or a digestion in the presence of both AspN and trypsin; and the least one peptide distinctive of G3m and/or IGHG3 alleles is selected from the group consisting of the peptides of SEQ ID NOs: 1 to 32 and any combination thereof.

According to yet another aspect, the present invention relates to the use of a plurality of peptides distinctive of G3m and/or IGHG3 alleles to calibrate a mass spectrometer used in a method according to the invention. Preferably, the plurality of peptides distinctive of G3m and/or IGHG3 alleles is selected from the group consisting of the peptides of SEQ ID NOs: 1 to 32 and any combination thereof.

According to a related aspect, the present invention provides a kit for the determination of the alleles of the IgG3s of an individual using a method according to the invention, and a kit for the diagnosis of a vertically transmitted infectious disease in a newborn according to the invention, each kit comprising a plurality of peptides disctintive of G3m and/or IGHG3 alleles belonging to the group consisting of the peptides of SEQ ID NOs: 1 to 32 and any combination thereof, wherein the peptides are intended to be used for calibrating the mass spectrometer used in the method.

These and other objects, advantages and features of the present invention will become apparent to those of ordinary skill in the art having read the following detailed description of the preferred embodiments.

BRIEF DESCRIPTION OF THE DRAWING

FIG. 2 is a list of the 32 discriminating peptides of G3m and/or IGHG3 alleles observable after theoretical cleavage by an AspN/trypsin combination of the heavy chain of the IgG3s and whose mass was determined for measurement using MALDI and ESI-ORBITRAP. The amino acids shown in bold are involved in the discrimination between the IGHG3 alleles included in the composition of the G3m alleles. The peptides are represented by showing the enzymatic cleavage sites by a point (".") and the amino acids before and after the enzymatic cleavages. A single cleavage fault is tolerated. The carbamidomethylated cysteines are shown as "C*". The m/z masses (Mox) are the masses calculated taking into account the possibility of oxidation of the methionine (M). The m/z masses determined with ESI-ORBITRAP are the masses of the bi-/tri-/and tetra-charged peptides.

FIG. 5 is a graph showing the relative abundance of the peptide WQQGNIFSCSVMHEALHNR in field samples. CI=blood from the mother, CO=umbilical cord blood, M=blood from the child at 3, 6 and 9 months; three technical repetitions of the experiment. (A) The peptide signals were measured by LTQ ORBITRAP and the relative abundance was calculated by the Progenesis LC-MS software. (B) The peptide signals were measured by SRM.

DETAILED DESCRIPTION OF THE INVENTION

Figure 1:
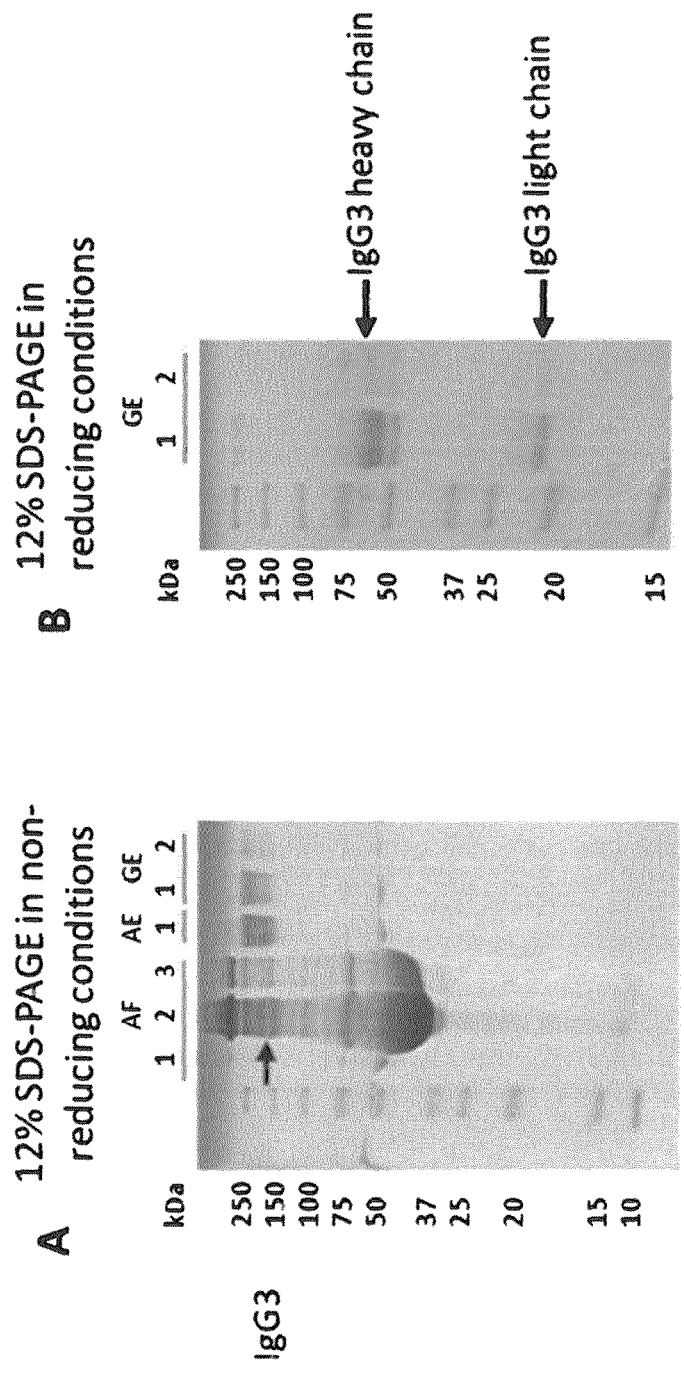
FIG. 1 shows the migration, on acrylamide gel, of the purification fractions obtained from passage of a plasma sample on the column of Protein A and then of Protein G. (A) 12% SDS-PAGE in non-reducing conditions. AF1 to AF3: Successive filtrate fractions of a Protein A column containing plasma proteins including IgG3s; AE: Elution fraction of a Protein A column containing IgG1, IgG2, IgG4; GE1 to GE2: Consecutive elution fractions of a Protein G column containing IgG3s. (B) 12% SDS-PAGE in reducing conditions. GE1 and GE2: Consecutive elution fractions of a Protein G column containing IgG3.

The present invention generally relates to a method for determining the polymorphism of IgG allotypes and other amino acid polymorphisms of the IgG heavy gamma chains in an individual. In particular, this method allows to distinguish and/or to quantify the immunoglobulins of a mother and of her newborn in a blood sample taken during the first months of the child's life. This method finds application in the area of diagnosis of vertically transmitted diseases in neonates.

I—Methods of Detecting Immunoglobulins of Neonates

As mentioned above, the presence, in the plasma of newborns, of maternal antibodies that are transmitted prenatally by active transport via the placenta precludes serological diagnoses in the infant. The transport of maternal antibodies during pregnancy is limited to the immunoglobulins G (IgG1, IgG2, IgG3 and IgG4). These immunoglobulins persist in the neonate for the first 6 months of life.

The methods of the invention are based on the use of the allotype polymorphisms or other amino acid polymorphisms of the heavy chains of immunoglobulins G for separately identifying and quantifying the immunoglobulins of the mother and those of the newborn in a blood sample obtained from the child. In the context of the present invention, the terms "neonate", "newborn" and "infant" are used interchangeably. These terms denote a human being during the first months of its life. The term "first months of life", as used herein, refers to a period from birth to the $9^{th}$ month (inclusive) after birth.

In the context of the present invention, the terms "immunoglobulin allotype" and "Gm allotype" are used interchangeably. The Gm allotypes (Lefranc and Lefranc, "The Human IgG Subclasses: Molecular analysis of structure, function and regulation", Pergamon Press, Oxford, 1990, pp. 43-78) are antigenic determinants localized on the heavy chains of three of the four IgG subclasses (IgG1, IgG2, IgG3 and IgG4) which allow distinction between individuals of the same species. They correspond, at the molecular level, to the substitution of one or more amino acids in the polypeptide sequence of the immunoglobulins.

The polymorphic Gm allotypes are encoded by alleles of genes that are closely related and inherited by particular combinations called haplotypes. The 11 Gm haplotypes that are known and their frequencies vary strongly from one population to another, thus defining four major groups: "African", "Asian", "European" and "European and Asian" (see Table 1).

TABLE 1

List of Gm haplotypes found in human populations.

| Population | Gm haplotypes |
|---|---|
| European | Gm 5, 10, 11, 13, 14, 26, 27; 3; . . . |
| | Gm 5, 10, 11, 13, 14, 26, 27; 3; 23 |
| European and Asian | Gm 21, 26, 27, 28; 1, 17; . . . |
| | Gm 21, 26, 27, 28; 1, 2, 17; . . . |
| African | Gm 5, 10, 11, 13, 14, 26, 27; 1, 17; . . . |
| | Gm 5, 6, 11, 24, 26; 1, 17; . . . |
| | Gm 5, 6, 10, 11, 14, 26, 27; 1, 17; . . . |
| | Gm 10, 11, 13, 15, 27; 1, 17; . . . |
| Asian | Gm 10, 11, 13, 15, 16, 27; 1, 17; . . . |
| | Gm 5, 10, 11, 13, 14, 26, 27; 1, 3; . . . |
| | Gm 5, 10, 11, 13, 14, 26, 27; 1, 3; 23 |

Gm allotypes of gamma1, gamma2 and gamma3 chains are presented in the order of the position in genes in sub-classes on the IGHG gene (G3, G1 and G2), with " ; " to separate the sub-classes and " , " to separate the allotypes. " . . . " designates the absence of G2m allotype.

The Gm system is composed of 18 allotypes (see Table 2). IgG3 is the most polymorphic human IgG subclass with 13 G3m allotypes located on the CH2 domains (n=6) and CH3 domains (n=7) of the gamma3 heavy chains, the combination of which leads to 6 major G3m alleles (encoded by one or several IGHG3 alleles). Amino acid changes resulting in extensive sequencing previously led to the definition of 19 IGHG3 alleles that have been correlated to the G3m alleles.

Consequently, preferably, a method according to the invention is based on the identification, by mass spectrometry, of the allotypes of the IgG3s present in a blood sample from the neonate (or of other polymorphic amino acids of the gamma chains of the IgG3s), and therefore comprises the determination, by mass spectrometry, of the G3m and IGHG3 alleles present in the blood sample obtained from the newborn.

However, as will be recognized by one skilled in the art, it is also conceivable to develop a method of detection according to the invention comprising the determination, by mass spectrometry, of the allotypes of the IgG1s or of the IgG2s, or other polymorphic amino acids of the gamma chains of the IgG1s or of the IgG3s, present in a blood sample from the neonate. Alternatively, it is also conceivable to develop a method of detection according to the invention comprising the determination, by mass spectrometry, of the allotypes of the IgG3s and of the IgG1s (or other polymorphic amino acids of the gamma chains of the IgG3s and of the IgG1s), or of the allotypes of the IgG3s and of the IgG2s (or other polymorphic amino acids of the gamma chains of the IgG3s and of the IgG2s), or of the allotypes of the IgG1s, IgG2s and IgG3s (or other polymorphic amino acids of the gamma chains of the IgG1s, IgG2s and IgG3s), present in a blood sample from the neonate.

TABLE 2

Localization of Gm allotypes on the three sub-classes of immunoglobulins G.

| | Localization | |
|---|---|---|
| Sub-class of IgG | Constant Domain | Allotype |
| IgG1 | CH3 | G1m(1) |
| | CH3 | G1m(2) |
| | CH1 | G1m(3) |
| | CH1 | G1m(17) |
| IgG2 | CH2 | G2m(23) |
| IgG3 | CH2 | G3m(5) |
| | CH3 | G3m(6) |
| | CH3 | G3m(10) |
| | CH3 | G3m(11) |
| | CH3 | G3m(13) |
| | CH2 | G3m(14) |
| | CH2 | G3m(15) |
| | CH2 | G3m(16) |
| | CH2 | G3m(21) |
| | CH3 | G3m(24) |
| | CH2 | G3m(26) |
| | CH3 | G3m(27) |
| | CH3 | G3m(28) |

Peptides Distinctive of G3m and/or IGHG3 Alleles

The methods of the invention are based on the detection, and optionally on the quantification, in the sample from the newborn, of peptides distinctive of Gm and/or IGHG alleles. In particular, in some preferred embodiments, a method according to the invention comprises the detection of one or more peptides distinctive of G3m and/or IGHG3 alleles.

The terms "peptide distinctive of G3m and/or IGHG3 alleles", "peptide discriminatory of G3m and/or IGHG3 alleles", "peptide marker of G3m and/or IGHG3 alleles" and "peptide specific of G3m and/or IGHG3 alleles" are used here interchangeably. They refer to a proteotypic peptide that is indicative (or that is a signature) of the identity of a G3m allele and/or an IGHG3 allele. A "proteotypic peptide" is a peptide that is generated by enzymatic digestion of a given protein in a reproducible and specific manner with respect to the protein and which can be detected by mass spectrometry.

As described in the Examples, a list of peptides distinctive of G3m and/or IGHG3 alleles was established by theoretical cleavage of the heavy chain of IgG3 by a combination of the endoproteinase AspN and of trypsin and identification of the proteotypic peptides specific to IGHG3 and discriminatory with respect to the alleles. These peptides are:

| | |
|---|---|
| TKPWEEQYNSTFR, | (SEQ ID NO: 1) |
| TKPREEQYNSTFR, | (SEQ ID NO: 2) |
| LREEQYNSTFR, | (SEQ ID NO: 3) |
| DGVEVHNAKTKPWEEQYNSTFR, | (SEQ ID NO: 4) |
| EEQYNSTFRVVSVLTVLHQ, | (SEQ ID NO: 5) |
| EEQYNSTFRVVSVLTVVHQ, | (SEQ ID NO: 6) |
| TKPWEEQYNSTFRVVSVLTVLHQ, | (SEQ ID NO: 7) |
| GFYPSDIAVEWESSGQPENNYK, | (SEQ ID NO: 8) |
| GFYPSDIAMEWESSGQPENNYK, | (SEQ ID NO: 9) |
| GFYPSDIAVEWESSGQPENNYNTTPPML, | (SEQ ID NO: 10) |
| GFYPSDIAVEWESSGQPNNNYNTTPPML, | (SEQ ID NO: 11) |
| GFYPSDIAVEWESSGQPENNYNTTPPVL, | (SEQ ID NO: 12) |
| GFYPSDIAVEWESNGQPENNYNTTPPML, | (SEQ ID NO: 13) |
| DIAVEWESSGQPENNYK, | (SEQ ID NO: 14) |
| DIAMEWESSGQPENNYK, | (SEQ ID NO: 15) |
| DIAVEWESSGQPENNYNTTPPML, | (SEQ ID NO: 16) |
| DIAVEWESSGQPNNNYNTTPPML, | (SEQ ID NO: 17) |
| DIAVEWESSGQPENNYNTTPPVL, | (SEQ ID NO: 18) |
| DIAVEWESNGQPENNYNTTPPML, | (SEQ ID NO: 19) |
| SRWQQGNIFSC$^c$SVMHEALHNHYTQK, | (SEQ ID NO: 20) |
| SRWQQGNIFSC$^c$SVMHEALHNR, | (SEQ ID NO: 21) |
| SRWQEGNVFSC$^c$SVMHEALHNR, | (SEQ ID NO: 22) |
| SRWQEGNIFSC$^c$SVMHEALHNR, | (SEQ ID NO: 23) |
| WQQGNIFSC$^c$SVMHEALHNHYTQK, | (SEQ ID NO: 24) |
| WQQGNIFSC$^c$SVMHEALHNR, | (SEQ ID NO: 25) |
| WQEGNVFSC$^c$SVMHEALHNR, | (SEQ ID NO: 26) |
| WQEGNIFSC$^c$SVMHEALHNR, | (SEQ ID NO: 27) |
| WQQGNIFSC$^c$SVMHEALHNHYTQKSLSLSPGK, | (SEQ ID NO: 28) |
| WQQGNIFSC$^c$SVMHEALHNRFTQK, | (SEQ ID NO: 29) |
| WQEGNVFSC$^c$SVMHEALHNRFTQK, | (SEQ ID NO: 30) |
| WQEGNIFSC$^c$SVMHEALHNRFTQK, and | (SEQ ID NO: 31) |
| WQQGNIFSC$^c$SVMHEALHNRYTQK, | (SEQ ID NO: 32) | wherein $C^c$ represents a carbamidomethylated cysteine.

The present invention therefore relates to a plurality of peptides distinctive of G3m and/or IGHG3 alleles selected from the group consisting of the peptides listed below or any combination of these peptides.

The present invention also relates to the use of these peptides in a method according to the invention.

As will be recognized by one skilled in the art, a different list of peptides distinctive of G3m and/or IGHG3 alleles could be established by a method similar to that used by the inventors but based on enzymatic cleavage using a different enzyme or a different combination of enzymes. In embodiments in which a method according to the invention is used for determining G1m and IGHG1 alleles or G2m and IGHG2 alleles, a list of peptides distinctive of G1m and/or IGHG1 alleles (i.e., distinctive of the IgG1 heavy chain) or of G2m and/or IGHG2 alleles (i.e., distinctive of the IgG2 heavy chain) could be obtained using a similar method.

Sample Preparation

The methods according to the invention are carried out using a blood sample from the neonate. Generally, a plasma sample is obtained from the blood sample. Methods for obtaining plasma from human blood are known in the art.

As noted above, a blood (or plasma) sample from a newborn comprises IgGs from the newborn and IgGs of maternal origin transmitted in utero. The "IgGs from the newborn" include fetal IgGs (i.e., IgGs synthesized by the fetus during pregnancy) and IgGs synthesized by the newborn after birth.

In certain embodiments, the methods according to the invention are carried out on a single subclass of immunoglobulins among IgG1, IgG2 and IgG3. In some preferred embodiments of the invention, the methods are carried out on the IgG3s present in the blood or plasma sample from the newborn.

In certain embodiments, the analysis by mass spectrometry is carried out on the blood or plasma sample. However, in certain preferred embodiments, before analysis by mass spectrometry, the IgG3s present in the blood or plasma sample are isolated and then submitted to enzymatic digestion.

The step of isolating the IgG3s can be performed by any suitable method; the isolation method used is not a critical or limiting element. For example, the IgG3s may be isolated by affinity chromatography. As described in the Examples presented below, it is for example possible to isolate the IgG3s from a plasma sample by carrying out affinity chromatography on a column of Protein A and/or affinity chromatography on a column of Protein G. Protein A and Protein G columns are available commercially, and one skilled in the art is able to select the appropriate elution conditions for obtaining purified or substantially purified IgG3s.

Alternatively or additionally, the IgG3s may be isolated by liquid chromatography, for example by fast protein liquid chromatography. The system for fast protein liquid chromatography or FPLC (Sheehan et al., Meth. Mol. Biol., 2004, 244: 253-258) was developed by Pharmacia (now GE Healthcare) in 1982 for separating or purifying proteins or other macromolecules from complex mixtures. The FPLC apparatus (AKTA$_{FPLC}$™ and BioLogic Duoflow™) is currently marketed by GE Healthcare and Bio-Rad Laboratories. The columns used in FPLC can separate macromolecules according to their size, their charge distribution, their hydrophobicity, or by affinity. A method of separation using the FPLC technique may allow standardization of the purification of IgG3s and optimization of the amount of purified IgG3s recovered.

After isolation, the IgG3s are submitted to a treatment for obtaining a mixture of proteolytic peptides of IgG3 comprising proteotypic peptides of IgG3 (i.e., peptides generated by enzymatic digestion in a reproducible and specific manner with respect to the immunoglobulins G3). The terms "proteolysis" and "enzymatic digestion" are used here interchangeably. They refer to the fragmenting or cutting of a protein into several pieces (peptides) under the action of an enzyme or of a combination of enzymes. As will be recognized by one skilled in the art, the method of enzymatic digestion used will have to be modelled on the conditions of theoretical enzymatic cleavage used for identifying the peptides distinctive of G3m and/or IGHG3 alleles.

In some preferred embodiments, the proteolysis of the IgG3s isolated from the neonate blood sample is therefore be carried out by digestion in the presence of endoproteinase AspN followed by digestion in the presence of trypsin, or by digestion in the presence of endoproteinase AspN and of trypsin.

Preferably, before digestion, the IgG3s are submitted to reduction, for example in the presence of dithiothreitol (DTT), which reduces the disulphide bonds of the immunoglobulins to thiols and thus separates the heavy chains from the light chains, and then to protection of the thiol groups of the heavy chain of IgG3, for example by alkylation in the presence of chloroacetamide.

Analysis by Mass Spectrometry

The determination of IgG heavy chains amino acid polymorphisms according to a method of the invention is carried out by mass spectrometry. Mass spectrometry is a physical technique of analysis for detecting and identifying molecules of interest by measuring their mass, characterizing their chemical structure, and optionally quantifying them. The principle of mass spectrometry is based on the gas phase separation of charged molecules (ions) as a function of their mass/charge ratio (m/z).

In a method according to the invention, analysis by mass spectrometry can be performed using any suitable technique of mass spectrometry allowing for peptides to be detected in a complex mixture and for their sequences to be inferred.

The sample comprising the mixture of proteolytic peptides of IgG3 can be introduced directly into the mass spectrometer in liquid or solid form (e.g., deposition on a MALDI plate) or by coupling the mass spectrometer to a separative method (e.g., liquid chromatography, capillary electrophoresis).

After they are introduced into the mass spectrometer, the peptides of the mixture are vaporized and ionized (the ionization source can be used either in positive mode for studying positive ions, or in negative mode for studying negative ions). There are various ionization methods, the most suitable methods in the context of the invention being electrospray ionization (ESI) and matrix-assisted laser desorption ionization (MALDI). The ions are then separated by an analyzer as a function of their mass/charge ratio (m/z). Preferably, the analyzer is a high-resolution analyzer that provides accurate measurement of the monoisotopic mass of an ion and then infers its composition after fragmentation. A high-resolution analyzer can be time-of-flight (TOF), Fourier transform ion cyclotron resonance (FTICR), the linear trap quadrupole Orbitrap (LTQ-Orbitrap) or a quadrupole filter (QqQ). These analyzers can be coupled together for conducting tandem mass spectrometry experiments (MS/MS). In tandem mass spectrometry, a first analyzer separates the ions, a collision cell fragments the ions, and a second analyzer separates the fragmented ions. Certain analyzers, such as the LTQ-Orbitrap, provide for ion fragmentation and direct analysis of the fragments.

In certain preferred embodiments of the invention, the mixture of proteolytic peptides of IgG3 is analyzed by a tandem mass spectrometry technique, for example MALDI in MS/MS mode, notably MALDI-TOF/TOF or electrospray in MS/MS mode (ESI-LTQ-Orbitrap). In certain preferred embodiments, the mass spectrometer is coupled to a nano-liquid chromatography (nLC) system. The mass measurements of the peptides and of their respective fragments allow determination of the sequence of these fragments (manually or by means of specialized software).

In other preferred embodiments of the invention, the mixture of proteolytic peptides of IgG3 is analyzed by SRM (selected reaction monitoring) MS/MS. SRM is a method used in tandem mass spectrometry in which an ion of a particular mass is selected in the first stage of a tandem mass spectrometer and an ion product of a fragmentation reaction of the precursor ion is selected in the second mass spectrometer stage for detection.

Comparison with the Amino Acid Polymorphism of Maternal IgGs Heavy Chain

The purpose of mass spectrometry analysis is to detect, in the mixture of proteolytic peptides of IgG3, one or more peptides distinctive of G3m and/or IGHG3 alleles, and thus determine the alleles of the IgG3s (i.e., the G3m and IGHG3 alleles) present in the neonate blood sample (see Table 4). However, since the sample from the newborn contains both IgG3s of the newborn and maternal IgG3s transmitted during pregnancy, it is necessary to compare the G3m and IGHG3 alleles determined for the IgG3s present in the newborn blood sample with the G3m and IGHG3 alleles of the IgG3s from the mother in order to deduce the G3m and IGHG3 alleles of the IgG3s of the newborn.

The G3m and IGHG3 alleles of the IgG3s present in a blood sample obtained from the mother can be determined by any suitable method.

In certain embodiments of the invention, this determination is carried out by means of an immunohaematologic technique, notably a technique of haemagglutination inhibition (Lefranc et al., Acta Anthropogenetica, 1976, 1: 34-45; Dugoujon et al., Vox Sanguinis, 1989, 57: 133-136; Field and Dugoujon, Gen. Epidemiol., 1989, 6: 31-33).

In other embodiments, the G3m and IGHG3 alleles of the IgG3s present in the mother's blood sample are determined by a method of the invention (see below).

II—Methods of Diagnosis of Vertically Transmitted Diseases

The methods of the invention for distinguishing the IgGs of the mother and those of the newborn in a blood sample taken during the first months of the child's life find application in the area of diagnosis of vertically transmitted diseases. The term "vertically transmitted disease" refers to any disease transmitted from the mother to the child during pregnancy, in particular infectious diseases. Infectious diseases that can be diagnosed using a method according to the invention include bacterial infectious diseases, viral infectious diseases, and parasitic infectious diseases. The diagnostic methods according to the invention are particularly interesting when the available methods for detecting the antigen of viral, parasitic or bacterial origin are not reliable.

In certain embodiments, a method according to the invention is used for diagnosing a parasitic infectious disease in a neonate, in particular a parasitic disease caused by a protozoan. Examples of parasitic diseases that can be diagnosed by a method of the invention include, but are not limited to, malaria; toxoplasmosis; Chagas disease; sleeping sickness—also called African trypanosomiasis—which is caused by a flagellate protozoan, *Trypanosoma brucei* ssp. *gambiense* or *Trypanosoma brucei* ssp. *Rhodesiense; babesioses*, which are rare diseases related to malaria and caused by a protozoan of the genus *Babesia* (*B. divergens, B. microti*); and leishmaniases, which result from infection with flagellate protozoa belonging to the genus *Leishmania*. In certain preferred embodiments, a method of the invention is used for diagnosing malaria, toxoplasmosis, Chagas disease or sleeping sickness.

In other embodiments, a method according to the invention is used for diagnosing a bacterial infectious disease in a neonate. Examples of congenital fetopathies of a bacterial nature that can be diagnosed by a method of the invention include, but are not limited to, infections by *streptococcus* B (streptococcosis), *Listeria monocytogenes* (listeriosis), *Treponema pallidum* (syphilis), *Chlamydia trachomatis* (chlamydiosis) or mycoplasma infections.

In yet other embodiments, a method according to the invention is used for diagnosing a viral infectious disease in a neonate. Examples of congenital fetopathies of a viral nature that can be diagnosed by a method of the invention include, but are not limited to, rubella, chickenpox, and infections with Parvovirus B19 (erythema infectiosum), cytomegalovirus (cytomegalic inclusion disease), or with herpes simplex virus.

When a method of the invention is used for diagnosing an infectious disease, it is carried out as described above, but on the pathogen-specific IgG3s (parasite, virus or bacterium) responsible for the disease to be diagnosed rather than on the total IgG3s. The terms "paratite-specific IgG3s", "virus-specific IgG3s" and "bacterium-specific IgG3s" denote the immunoglobulins G3 that are produced by the immune system of the human body in response to the parasitic, viral and bacterial pathogen, respectively. The diagnostic techniques according to the invention therefore require a step of isolation of the pathogen-specific IgG3s present in the neonate blood sample to be tested.

The pathogen-specific IgG3s may be isolated by any suitable method known in the art. For example, said isolation may be performed via formation of an immune complex (i.e., an antigen-antibody complex) resulting from contact between purified IgG3s with a specific antigenic preparation. After washing to remove any IgG3 not bound to the antigen (i.e., not complexed and therefore not pathogen specific), the immune complexes can be dissociated to recover the IgG3s specific to the pathogen, for example by application of an acidic buffer solution.

In the methods for the diagnosis of Chagas disease according to the invention, the antigenic preparation used for isolating the pathogen-specific IgG3s can be a parasitic extract of *Trypanosoma cruzi* obtained by lysis of an exponential culture of epimastigotes in fetal calf serum (Flechas et al., BMC Infectious Diseases, 2009, 9: 186).

In the methods for the diagnosis of toxoplasmosis according to the invention, the antigenic preparation used for isolating the pathogen-specific IgG3s can be a soluble parasitic extract of *Toxoplasma gondii* obtained from an in vitro culture of tachyzoites in murine cells (Fatoohi et al., Clin. Diag. Lab. Immunol., 2001, 9: 704-707).

In the methods for the diagnosis of malaria according to the present invention, the antigenic preparation used for isolating the pathogen-specific IgG3s can be a recombinant Protein AMA1 (Apical Membrane Protein 1) of the asexual blood stages of *Plasmodium falciparum* (Nebie et al., Infection and Immunity, 2008, 76: 759-766). Alternatively, the antigenic preparation may be a parasitic extract of *P. falciparum* obtained from an in vitro culture of a parasitic line enriched to more than 50% of schizonts (Fievet et al., Am. J. Trop. Med. Hyg., 1995, 53: 612-617).

A method of diagnosis according to the invention is therefore carried out as described above except that it is performed on the IgG3s specific of the pathogen responsible for the disease to be diagnosed and not on the total IgG3s. In certain embodiments, in particular when small amounts of IgG3s specific to the pathogen are obtained, a selective and sensitive technique of mass spectrometry, MRM (Multiple Reaction Monitoring), also called SRM (Selected Reaction Monitoring), can be used. As already mentioned above, this operating mode of mass spectrometry offers double selectivity, in selection of the parent ion and of the fragment ion produced.

The "pathogen-specific IgG3s of the newborn" isolated from the blood sample comprise pathogen-specific IgG3s of maternal origin and transmitted during pregnancy and, if congenital transmission has occurred, pathogen-specific IgG3s synthesized by the fetus. They can optionally contain pathogen-specific IgG3s synthesized by the newborn in response to exposure to the pathogen after birth.

In a method of diagnosis according to the invention, the G3m and IGHG3 alleles of the pathogen-specific IgG3s isolated from a newborn blood sample determined by mass spectrometry are compared to the G3m and IGHG3 alleles of the IgG3s of the mother. As described above, the allotypes of the IgG3s of the mother can be determined by a classical method of immunohaematology or by a method according to the present invention. The determination of the G3m allotypes of the mother can be performed on the total IgG3s or on the pathogen-specific IgG3s, and both determinations should lead to the same result since the polymorphisms are located on the constant domains of the gamma3 heavy chains.

As will be recognized by one skilled in the art, the definitive diagnosis of the congenital disease may be based solely on a method of diagnosis according to the invention. Alternatively, a clinical diagnosis may be established based on the results of a method according to the invention combined with the results of other methods of diagnosis (for example, microscopic observation of the parasite in a newborn blood sample or amplification of portions of genes of the pathogen by PCR). Armed with a definitive diagnosis, the physician can make an informed decision to initiate drug treatment for the newborn, to interrupt drug treatment administered preemptively, or to continue said treatment.

III—Methods of Determining Polymorphism of G3m and IGHG3 Alleles

As will be recognized by one skilled in the art, a method according to the invention may be used for determining the Gm and IGHG alleles of the IgGs of an individual at any stage of life, i.e., aside from any consideration of the problems connected with the diagnosis of vertically transmitted diseases in newborns. This is all the more important that the classical method for determining Gm allotypes, which is a serological method of haemagglutination inhibition using erythrocytes of blood group 0 Rh+ coupled to anti-Rh antibodies of known Gm allotypes and to monospecific anti-allotype antibodies, will soon no longer be available. Indeed, the collections of monospecific anti-allotype and anti-RhD sera, which in the past were obtained from pregnant women and from blood donations, are practically exhausted.

The present invention therefore also relates to a method for determining the Gm and IGHG alleles of IgGs of an individual, the method comprising a step of: determining, by mass spectrometry, the G3m and IGHG3 alleles of the IgG3s present in a blood sample from the individual. Preferably, the method comprises: isolation of the IgG3s present in the blood sample; proteolysis of the IgG3s isolated to obtain a mixture of proteolytic peptides of IgG3; and detecting, by mass spectrometry, in the mixture of proteolytic peptides of IgG3, the presence of at least one peptide distinctive of G3m and/or IGHG3 alleles in order to determine the G3m and IGHG3 alleles of the IgG3s of the individual. In some preferred embodiments, the peptides distinctive of G3m and/or IGHG3 alleles belong to the group consisting of the peptides of sequence SEQ ID NO: 1 to 32; and the proteolysis of the IgG3s is carried out in the presence of endoproteinase AspN and trypsin.

The term "individual", as used in the context of the present invention, refers to a human being who has passed the infant stage, i.e., a human being more than 6 or 9 months of age (when the immunoglobulins transmitted from the mother have been eliminated completely).

The steps of isolation and of proteolysis of the IgG3s may be carried out as described above.

The description of the present invention focuses on the determination of the allotypes, or other amino acid polymorphisms, of IgG3s, but, as pointed out above, it is also conceivable to develop a method according to the invention comprising the determination, by mass spectrometry, of the allotypes, or other amino acid polymorphisms, of IgG1s' or of IgG2s' gamma chains of an individual. Alternatively, it is also possible to develop a method according to the invention comprising the determination, by mass spectrometry, of the allotypes, or other amino acid polymorphisms, of IgG3s and IgG1s of an individual, or of the allotypes, or other amino acid polymorphisms, of IgG3s and IgG2s of an individual, or of the allotypes, or other amino acid polymorphisms, of IgG1s, IgG2s and IgG3s of an individual.

IV—Kits

The present invention also provides kits comprising materials useful for carrying out a method according to the invention. In particular, the present invention provides a kit for determining the polymorphism of the heavy gamma chain of IgG3s of an individual and a kit for diagnosing a vertically transmitted disease in a neonate, in particular a congenital parasitic disease. In general, a kit according to the invention comprises a plurality of peptides distinctive of G3m and/or IGHG3 alleles belonging to the group consisting of the peptides of sequence SEQ ID NO: 1 to 32 and any combination of these peptides. These peptides will be used advantageously for calibrating the mass spectrometry apparatus used. Optionally, the kit can further comprise instructions for carrying out the mass spectrometer calibration. "Calibration", as used herein, refers to any procedure for adjusting or calibrating the mass spectrometer utilized in a method according to the invention.

In certain embodiments, the kit comprises all the peptides distinctive of G3m and IGHG3 alleles (SEQ ID NO: 1-32) and can therefore be used and marketed throughout the world. In other embodiments, the kit only comprises the peptides distinctive of G3m and/or IGHG3 alleles necessary for determining a haplotype of the "African" type or of the "Asian" type or of the "European" type for the geographically localized use and marketing of the kit.

The peptides distinctive of G3m and/or IGHG3 alleles useful for determining a haplotype of the "African" type are the peptides of sequence SEQ ID NO: 2, SEQ ID NO: 5-6, SEQ ID NO: 8-10, SEQ ID NO: 14-16, SEQ ID NO: 18, SEQ ID NO: 20-31, and any combination of these peptides.

The peptides distinctive of G3m and/or IGHG3 alleles useful for determining a haplotype of the "Asian" type are the peptides of sequence SEQ ID NO: 1-10, SEQ ID NO: 12-16, SEQ ID NO: 19-21, SEQ ID NO: 24-25, SEQ ID NO: 28-29, SEQ ID NO: 32, and any combination of these peptides.

The peptides distinctive of G3m and/or IGHG3 alleles useful for determining a haplotype of the "European" type are the peptides of sequence SEQ ID NO: 2-3, SEQ ID NO: 5-6, SEQ ID NO: 8, SEQ ID NO: 10, SEQ ID NO: 13-14, SEQ ID NO: 16, SEQ ID NO: 19, SEQ ID NO: 21, SEQ ID NO: 25, SEQ ID NO: 29, SEQ ID NO: 32, and any combination of these peptides.

The kit may further comprise reagents or solutions for preparing calibration samples. The various components of the kit may be supplied in solid form (for example in lyophilized form) or in liquid form. A kit can optionally include containers containing each of the reagents or solutions, and/or containers (test tubes, bottles, etc.) for carrying out preparation of the calibration samples.

The kit may also further comprise reagents for preparing the blood sample to be analyzed (e.g., reagents necessary for isolating the IgG3s, and/or reagents necessary for enzymatic digestion of the IgG3s, etc.). These reagents may be comprised in containers included in the kit.

Finally, the kit may further comprise a notice in the form prescribed by a governmental agency regulating the sale and use of products for medical or pharmaceutical use.

Unless they are defined otherwise, all technical and scientific terms used herein have the same meaning as that commonly understood by an ordinary specialist in the field to which this invention belongs. In addition, all the publications, patent applications, all the patents and all other references mentioned here are incorporated by reference.

The following examples and the drawings are presented to illustrate certain embodiments of the procedures described above and must in no case be regarded as limiting the scope of the invention.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Some of results presented below have been described in a scientific paper (C. Dechavanne et al., "Mass spectrometry detection of G3m and IGHG3 alleles and follow-up of differential mother and neonate IgG3"), which has been submitted to PLoS ONE on Jul. 30, 2012. The entire content of this paper is incorporated herein by reference.

Methods Used

1. Definition of the Theoretical List of the Peptides Distinctive of G3m and IGHG3 Alleles The list of proteotypic peptides was established based on a comparison of the peptide sequences of four IGHG proteins. The sequences were cleaved virtually by the endoproteinase AspN and trypsin with or without missing enzymatic cleavage. All the peptides obtained by theoretical enzymatic digestion were compared in order to determine those that are specific of IGHG3 and discriminatory with respect to alleles. A list was defined comprising 32 proteolytic peptides suitable for analysis using a MALDI-TOF/TOF technique or an Orbitrap technique or yet an SRM technique.

2. Plasma Samples Used in the Purification and Digestion Protocols

The samples analysed in this study came from two separate geographical regions: Europe and Africa. The European blood samples were obtained from adult volunteers in good health of French origin. Five (5) milliliters of blood were collected in Vacutainer® EDTA tubes. After centrifugation, 1 mL of fresh plasma was purified and aliquot fractions were prepared from the remaining plasma and were frozen at −20° C. for later use.

The African plasma samples were obtained during two studies carried out in Benin by the inventors' team. The first study, conducted in 2006-2007, related to 155 children mainly belonging to the Fon ethnic group (Migot-Nabias et al., J. Infect. Dis., 2008, 198: 1892-1895). Blood samples were collected in 5-mL Vacutainer® EDTA tubes, and after centrifugation, plasma samples were prepared and frozen at −20° C. In the second study, a cohort of 627 neonates in a semi-rural region in the south of Benin and their mothers was constituted and monitored from 2007 to 2010 (Le Port et al., in preparation). At birth, a blood sample from the mother as well as the cord blood were collected in Vacutainer® EDTA tubes. Then, a blood sample from each child was collected every three months up to the age of 18 months. The plasma samples were stored at −80° C. Samples obtained from the mother at the time of birth and from her child (cord blood and plasma samples obtained at 3, 6 and 9 months after birth) were used in the present study.

3. Serological Determination of the Gm Allotypes of Immunoglobulins

The Gm allotypes of the plasma specimens were analyzed by the standard qualitative method of haemagglutination inhibition (Dugoujon et al., Vox Sanguinis, 1989, 57: 133-136; Field and Dugoujon, Gen. Epidem., 1989, 6: 31-33). Briefly, erythrocytes of human blood of group O Rh+ were coated with anti-Rh antibodies of known Gm allotypes, plasma samples, and monospecific anti-allotype antibodies. After sedimentation, the plasma specimens containing IgGs of a particular allotype inhibit haemagglutination by the anti-allotype antibody whereas the plasma specimens that tested negative for the relevant IgG do not cause inhibition.

4. Purification of the Total IgG3s

The plasma obtained from freshly collected blood samples was purified directly and the samples of frozen plasma were used after centrifugation to remove the fibrin aggregates. A volume of 250 µL of plasma is sufficient for detecting and quantifying the peptides of the purified total IgG3s.

A column (HiTrap Protein A HP, GE Healthcare) of Protein A was used for the first purification step, which was carried out according to the supplier's instructions. This column is used for retaining the IgG1, IgG2 and IgG4 interfering immunoglobulins, allowing the IgG3 immunoglobulins to pass through into the filtrate. The retention of IgG1, IgG2 and IgG4 in the Protein A column requires low ionic strength, pH 7.

It is necessary to remove the other serum proteins from the filtrate fraction resulting from chromatography on the Protein A column and comprising the IgG3s. Therefore it was passed through a column of Protein G (Protein G Sepharose HP SpinTrap, GE Healthcare), which has strong affinity for the Fc fragments of the immunoglobulins regardless of class. The other serum proteins, not retained, were removed into the filtrate (FIG. 1). The IgG3s were retained in the column at neutral pH and the IgG3s were eluted on lowering the pH. The eluate was neutralized to preserve the quality of the labile immunoglobulins in an acid medium. The quality of purification was evaluated by ELISA against the various classes of IgG.

5. Reduction, Alkylation and Enzymatic Digestion

The reactions of reduction, alkylation and enzymatic digestion were carried out either in solution, or on bands of 12% acrylamide gel corresponding to the heavy chains of the IgGs after electrophoretic migration of the purified samples in reducing conditions. Several enzymes were tested, alone or combined, including: papain, GluC, PNGase, AspN and trypsin. The objective was to select the enzyme or enzymes enabling the largest number of G3m and IGHG3 allelic discriminatory peptide sequences to be contained within a range of masses accessible to high-resolution mass spectrometers. A combination of AspN and trypsin at a final concentration of 10 ng/µL gave the best result.

Using the Samples of IgG on SDS-PAGE Gels.

Fifteen (15) µL of a mixture (volume/volume) 2× β-mercaptoethanol/Laemmli buffer was added to 15 µL of the purified samples. After boiling at 100° C. for 5 minutes, the samples were transferred to a gel of 12% SDS-PAGE stained with Coomassie Blue. The 60 kDa bands corresponding to the heavy chain of the IgG were cut out. The samples of gels were decolorized with 50% acetonitrile, submitted to reduction in the presence of 20 mM of DTT for 30 minutes at 56° C., and to alkylation in the presence of 25 mM of chloroacetamide for 30 minutes at room temperature to protect the thiol groups of the proteins. After addition of 1 volume of acetonitrile to dehydrate the gel and removal of the supernatant, 1 µL of AspN (10 ng/mL, Roche) was added to the gel. The samples were incubated overnight at 30° C. or for 3 hours at 37° C. Additional digestion was carried out with 2 µL of freshly activated trypsin (10 ng/mL, Modified Sequencing Grade from Promega). The supernatants were collected and replaced with 10 µL of formic acid (4%) for 5 minutes at room temperature. After a step of sonication for 30 seconds, the supernatant was collected and replaced with 50% acetonitrile to dehydrate the gel and extract the peptides from the gel. At each step, the supernatants were collected, and fully dehydrated under vacuum. The samples were resuspended in a mixture of 10% acetonitrile and 0.1% trifluoroacetic acid (TFA).

Using the Samples of IgG in Solution.

DTT was added to a final concentration of 10 mM in 37 µL of purified sample in solution to reduce the disulphide bonds for 30 minutes at 56° C. Chloroacetamide was added to a concentration of 25 mM. AspN (1 µL, 10 ng/4) was added to the reaction mixture, incubated for 3 hours at 37° C. or overnight at 30° C. Freshly activated trypsin (2 µL, 10 ng/µL) was then added under the same incubation conditions. After reaction, trifluoroacetic acid (TFA, 20%, 1 µL) was added to stop the enzymatic digestion.

6 Analyses by MALDI Mass Spectrometry (MALDI-MS)

Nanochromatography.

The peptides of the samples obtained after enzymatic digestion were concentrated and separated by HPLC (Ultimate3000, Dionex). Briefly, 10 µL of eluate were injected in a C18 precolumn (Acclaim pepmap100 C18, particles of 5 µm, pore size 100 Å, inside diameter 300 µm, and length 5 mm). The peptides were then eluted (300 mL/min) to the analytical column (C18pepmap100, 3 µm particles, pore size 100 Å, inside diameter 75 µm and length 15 cm) with a gradient from 7% of solvent B (80% acetonitrile, 20% solvent A) at the moment of introduction of the peptides in the analytical column to 20% of solvent B in 7 minutes and from 20% of solvent B to 60% of solvent B in 58 minutes. The fractions were mixed in 1:9 ratio with 3 mg/mL of HCCA (Laser Biolabs) in 70% of acetonitrile (Carlo Erba), 0.1% of TFA (Pierce) and Glu-fibrinopeptide at 3 fmol/spot. In all, 192 fractions were collected and analysed using a 4800 MALDI TOF/TOF analyser (ABI).

MALDI Spectrometry.

Acquisition and processing of the mass spectra were carried out with the 4000 series explorer software (ABSciex, version 3.5.28193 build 1011) in positive reflectron mode at constant laser fluence with filtering of the low-mass ions, and delayed extraction. External calibration of the plate was performed using 4 calibration points distributed over the plate. In addition, internal calibration using Glu-fibrinopeptide gave a measurement accuracy below 10 ppm. For each fraction, 10 series of 50 spectra were recorded in the range from 700 to 4000 kDa at a laser frequency of 200 Hz. For each sample, the 500 raw spectra added were processed to obtain monoisotopic values from isotopic masses with signal/noise ratios of min. 20.

MALDI-MS/MS Spectrometry.

In each mass spectrum, the 8 most abundant peaks were selected for fragmentation beginning with the least abundant. The close precursors in a resolution of 200 were excluded. For each precursor, 1000 MS/MS spectra were added in increments of 50. The spectra were processed as follows: subtraction of the base line, Savitzky-Golay smoothing with 3 points on the peak and a polynomial order of 4. The lists of peaks reflect the monoisotopic values of the isotope clusters with a minimum signal/noise ratio of 22. The lists of peaks generated in MS/MS were then submitted to a Mascot internal search engine (Matrix science), version 2.2 to identify the peptides (see below).

LTQ-ORBITRAP MS and MS/MS Spectrometry.

The analyses were performed with a liquid chromatography system with fast separation (Ultimate 3000 RSLC, Dionex) coupled to a mass spectrometer (LTQ-Orbitrap Velos, Thermo Fisher Scientific). Briefly, the peptides obtained by enzymatic digestion were loaded on a reverse-phase precolumn (C18, 3 µm particles, pore size 100 Å, inside diameter 75 µm, and length 2 cm) with a loading solvent containing 98% water, 2% acetonitrile and 0.1% trifluoroacetic acid at 5 µL/minute. The peptides were separated on a reverse-phase analytical column (C18, 2 µm particles, pore size 100 Å, inside diameter 75 µm, and length 15 cm) with a gradient of 45 minutes ranging from 100% of solvent A (5% acetonitrile, 0.1% AF and 95% water) to 40% of solvent B (80% acetonitrile, 0.085% formic acid and 20% water).

The mass spectrometer (LTQ-Orbitrap) used acquired the data throughout the elution process and operated as follows: the MS scans were acquired with the Orbitrap, followed by up to 10 spectra of LTQ MS/MS CID on the most abundant precursors detected in the MS scans. Exclusion of latency was fixed at 24 seconds for the previously fragmented precursors. The settings used for the mass spectrometer were as follows: MS (AGC: $1 \times 10^6$, resolution: $3 \times 10^4$, m/z of 400-2000, maximum ion injection time: 1000 ms); MS/MS (AGC: $1 \times 10^4$, maximum ion injection time: 200 ms, minimum signal threshold: 2000, width of isolation: 2 Da). Fragmentation was permitted for precursors with a charge state of 2 or 3.

Processing the Spectra.

The software used for extracting the lists of peaks and generating the mgf (mascot generic file) files was Proteome discoverer 1.2 with a threshold value of signal to noise of 3.

Database Search.

The MS/MS spectra obtained by the two mass spectrometers were submitted to a Mascot internal search engine (Matrix science), version 2.2 to identify the peptides. The database searched was a "Parasitoswissprot" database developed internally (resulting from concatenation of the IgHG Immunoglobulin-variants database from IMGT with the *Plasmodium* fasta database "plasmoDB" and the Swissprot fasta database, i.e. in a total of 529942 sequences, 189364547 residues). The mass tolerance for the precursors was fixed at 20 ppm for MALDI and 3 ppm in Orbitrap. For the fragments, it was fixed at 0.45 Da, oxidation of the methionines was partially allowed and carbamidomethylation was considered complete. The search performed was not restricted to one species. The specificities of enzymatic cleavage defined were the combination of those of trypsin and of AspN. A filter was applied to the search so as to reduce the probability of false positives to less than 5% (minimum value of Mascot score of 25 for the peptides).

Semi-Quantitative Information without Labelling.

The Progenesis software (Version 3.0; Nonlinear Dynamics Ltd.) was used for quantifying the variation of the discriminating peptides based on the retention time, the m/z ratio and the peak intensity (peak area) of the samples. The Progenesis software processes the raw data files obtained from the Orbitrap in two steps: alignment followed by normalizing. The data file that led to the largest number of characteristics (1:1 ratio) was used as reference, for aligning the retention time with the other measurements. The experimental variations were corrected by calculating the robust distribution of all the ratios (log(ratio)). The chromatographic peaks (the events) were converted to a list of intensities and retention times using the raw data files. The data were filtered, conserving the events according to the following criteria: mass/charge ratio in the range 300-1700, retention time 8-25 minutes, and charge state from 2 to 4.

A matrix of all the samples, consisting of all the masses corresponding to the intensities of the peaks of each sample, was generated. Mascot generic files (mgf) were exported from Progenesis and imported into Mascot software; and the Parasitoswissprot database was interrogated (taxonomy: mammals, enzyme: AspN+trypsin, fixed modification: carbamidomethylation, variable modification: oxidation, number of missing cleavages allowed: up to 2, peptide tolerance: +/−5 ppm, MS/MS tolerance: +/−0.45 Da, peptide charge: 2+ 3+ or 4+). The resultant XML files were imported into Progenesis for assigning a peptide to the events. The normalized abundances of the peptides were analysed using Excel software.

Selected Reaction Monitoring (SRM) on Triple Quadrupole Mass Spectrometry.

Analyses were performed using an Ultimate 3000 SRLC (Dionex, The Netherlands) coupled to a TSQ Vantage™ mass spectrometer (Thermo Fisher Scientific, San Jose, Calif.) in ESI mode. Briefly, the peptides were loaded and washed on a C18-reverse precolumn (PepMap C18, 3 µm, 100 Å, 75 µm i.d., 2 cm length) using a loading buffer containing H2O/CAN/TFA 98:2:0.05 (v/v/v) at 6 µL/minutes. The peptides were then separated on a C18-reverse phase analytical column (PepMap C18 2 µm, 100 Å, 75 µm i.d., 15 cm length) with a 60 min gradient from 99% A (H2O/ACN/formic acid 98:2:0.1 (v/v/v)) to 50% B (H2O/ACN/formic acid 10:90:0.1 (v/v/v)) at 300 nl/min. All the data were acquired in triplicate and blank runs were interposed until necessary to avoid peptide carry-over effects.

SRM acquisitions were performed in scheduled mode. The SRM transitions (precursor/product pairs) were recorded at the retention time+/−4 minutes as measured during the optimization step. In the most complex part of the chromatogram, where transitions overlap the most, the dwell time associated to the SRM method was less than 2 seconds. The first and third quadrupole were set to 0.7 Da peak width. For all the transitions related to the WQQGNIFSCSVMHEALHNR and WQEGNVFSCSVMHEALHNR peptides, dwell time of 100 ms was used. The sensitivity threshold tested with AQUA peptides was 10 fmol of injected peptide. SRM data processing and absolute quantitation using AQUA peptides were performed by Pinpoint version 1.2 (Thermo Fisher, Germany).

RESULTS

1. Serological Determination of the Gm Allotypes of the Plasma Samples

The French individual has a phenotype Gm5,10,11,13,14,26,27;3 comprising the alleles G3 m5,10,11,13,14,26,27 and G1m3, which are commonly associated with the Gm haplotypes of individuals of European origin.

Two children in Benin from a previous study (Migot-Nabias et al., J. Infect. Dis., 2008, 198: 1892-1895), homozygous for the alleles G3 m5,10,11,13,14,26,27 (individual AS20, phenotype Gm5,10,11,13,14,26,27;1,17) and G3 m5,6,11,24,26 (individual NP47, phenotype Gm5,6,11,24,26;1,17), which are commonly expressed in sub-Saharan populations, were selected.

The plasma samples from a mother and her child were selected from a multidisciplinary study on malaria carried out in Benin in 2007-2010. Serological determination identified a phenotype Gm5,6,10,11,13,14,24,26,27,28;1,17 for the mother (individual A170M) and a phenotype Gm5,10,11,13,14,26,27;1,17 for the child (serological determination carried out on the plasma from A170M15 collected at age 15 months). Based on serological determination of the father (individual A170P, Gm5,10,11,13,14,15,26,27,28;1,17), it was concluded that the mother was G3m heterozygous (G3 m5,10,11,13,14,26,27/G3 m5,6,11,24,26,28) and her child was homozygous for G3 m5,10,11,13,14,26,27.

2. Purification of the IgG3s of a Plasma Sample Obtained from a French Individual All the fractions resulting from affinity chromatography on columns of Protein A and of Protein G were transferred to a 12% SDS-PAGE gel (FIG. 1) and then assayed by ELISA (Enzyme-Linked Immunosorbent Assay) to measure the amounts of each subclass of immunoglobulins throughout the purification operation.

On the unreduced gel, the fraction AF (3 wells) consisted of IgG3 with a band at about 160 kDa and of several other plasma proteins, which are represented by the other bands. In the fraction AE, the IgG1, IgG2 and IgG4 and other plasma proteins were eluted. The fraction GE (2 wells) contained contamination with plasma proteins. Washing of these fractions (3 wells) removed most of the contaminating proteins.

On the reduced gel, the first eluate GE1 from the column of Protein G was contaminated with plasma proteins but the IgGs were present predominantly. The fractions from washing (3 wells) had a band of 60 kDa. It is possible that certain immunoglobulins were lost during the washing steps.

Application of an ELISA assay for all the fractions confirmed these observations (Table 3): the IgG3s were released from fractions AE and GF; contamination with other IgG subclasses took place in fractions GE; the eluates GE1 and GE2 were composed of IgG1 (22.7%), IgG2 (2%), IgG3 (29%) and IgG4 (46.3%). Purification by chromatography on a column of Protein A eluted 95% of IgG3.

TABLE 3

ELISA assay of the IgG subclasses contained in the purification fractions obtained from passage of a plasma sample on columns of Protein A and then Protein G.

| Fractions | IgG1 (AU) | IgG2 (AU) | IgG3 (AU) | IgG4 (AU) |
|---|---|---|---|---|
| AE1 | 91.3 | 103.8 | 89.5 | 0 |
| AE2 | 133.0 | 106.6 | 214.8 | 972.6 |
| AE3 | 113.3 | 106.5 | 152.7 | 640.3 |
| AE4 | 90.9 | 64.8 | 0 | 0 |
| AE5 | 74.9 | 31.2 | 0 | 0 |
| GF1 | 65.8 | 57.0 | 101.1 | 0 |
| GF2 | 0 | 0 | 93.7 | 0 |
| GF3 | 0 | 0 | 100.5 | 0 |
| GF4 | 0 | 57.8 | 99.2 | 0 |
| GF5 | 0 | 0 | 90.4 | 0 |
| GF6 | 0 | 99.5 | 30.9 | 0 |
| GF7 | 0 | 0 | 0 | 0 |
| GE1 | 135.8 | 0 | 0 | 0 |
| GE2 | 0 | 11.8 | 173.5 | 276.5 |
| GE3 | 0 | 22.6 | 100 | 0 |
| GE4 | 0 | 0 | 0 | 0 |

Results expressed in Arbitrary Units (AU);
AE: Elution fractions from purification on Protein A column containing IgG1, IgG2, IgG4;
GF: Filtrate fractions from purification on Protein G column containing plasma proteins;
GE: Elution fractions from purification on Protein G column containing IgG3.

In conclusion, the Protein A and Protein G columns can purify the majority of the IgG3s. The results from mass spectrometry showed that contamination with IgG subclasses interferes with measurement of the IgG3 peptides.

Nevertheless, the list of peptides distinctive of G3m and IGHG3 alleles presented in Table 4 below was specifically representative of IgG3 among other IgG subclasses and counterbalanced this handicap.

TABLE 4

List of the 32 peptides distinctive of IGHG3 alleles observable after theoretical cleavage of the heavy chain of the IgG3s by an AspN/trypsin combination.

| Proteotypic Peptides | IGHG3 Alleles |
|---|---|
| CH2 domain | |
| TKPWEEQYNSTFR | *18, *19 |
| TKPREEQYNSTFR | *01 à *10, *13, *17 |
| LREEQYNSTFR | *14 à *16 |
| DGVEVHNAKTKPWEEQYNSTFR | *18, *19 |
| EEQYNSTFRVVSVLTVLHQ | *01 à *08, *10, *13 à *17 |
| EEQYNSTFRVVSVLTVVHQ | *09 |
| TKPWEEQYNSTFRVVSVLTVLHQ | *18, *19 |
| CH3 domain | |
| GFYPSDIAVEWESSGQPENNYK | *06, *07 |
| GFYPSDIAMEWESSGQPENNYK | *17, *18, *19 |
| GFYPSDIAVEWESSGQPENNYNTTPPML | *01, *04, *05, *09 à *13 |
| GFYPSDIAVEWESSGQPNNNYNTTPPML | *02 |
| GFYPSDIAVEWESSGQPENNYNTTPPVL | *03 |
| GFYPSDIAVEWESNGQPENNYNTTPPML | *08, *14 à *16 |
| DIAVEWESSGQPENNYK | *06, *07 |
| DIAMEWESSGQPENNYK | *17, *18, *19 |
| DIAVEWESSGQPENNYNTTPPML | *01, *04, *05, *09 à *13 |
| DIAVEWESSGQPNNNYNTTPPML | *02 |
| DIAVEWESSGQPENNYNTTPPVL | *03 |
| DIAVEWESNGQPENNYNTTPPML | *08, *14 à *16 |
| SRWQQGNIFSC$^c$SVMHEALHNHYTQK | *17 à *19 |
| SRWQQGNIFSC$^c$SVMHEALHNR | *01, *02, *06 à *12, *14 à *16 |
| SRWQEGNVFSC$^c$SVMHEALHNR | *03 |
| SRWQEGNIFSC$^c$SVMHEALHNR | *13 |
| WQQGNIFSC$^c$SVMHEALHNHYTQK | *17 à *19 |
| WQQGNIFSC$^c$SVMHEALHNR | *01, *02, *06 à *12, *14 à *16 |
| WQEGNVFSC$^c$SVMHEALHNR | *03 |
| WQEGNIFSC$^c$SVMHEALHNR | *13 |
| WQQGNIFSC$^c$SVMHEALHNHYTQKSLSLSPGK | *17 à *19 |
| WQQGNIFSC$^c$SVMHEALHNRFTQK | *01, *02, *06 à *12 |
| WQEGNVFSC$^c$SVMHEALHNRFTQK | *03 |
| WQEGNIFSC$^c$SVMHEALHNRFTQK | *13 |
| WQQGNIFSC$^c$SVMHEALHNRYTQK | *14 à *16 |

The amino acids shown in bold are implicated in the discrimination between the IGHG3 alleles included in the composition of the G3m alleles; and C$^c$ represents a carbamidomethylated cysteine.

3. List of the Peptides Distinctive of G3m and IGHG3 Alleles

The 32 proteolytic peptides suitable for an analysis using a MALDI-TOF/TOF or Orbitrap technique identified theoretically as described above are presented in Table 4 with the IGHG3 alleles of which they are distinctive, and Table 5 below shows the correspondence between the IGHG3 alleles and the G3m alleles.

TABLE 5

Correspondence between the IGHG3 alleles and the G3m alleles.

| IGHG3 Alleles | G3m Alleles Complete Nomenclature | G3m Alleles Simplifed Nomenclature |
|---|---|---|
| IGHG3*01, IGHG3*05, IGHG3*06, IGHG3*07, IGHG3*09, IGHG3*10, IGHG3*11, IGHG3*12 | G3m5, 10, 11, 13, 14, 26, 27 | G3m5* |
| IGHG3*13 | G3m5, 6, 10, 11, 14, 26, 27 | G3m6* |
| IGHG3*03 | G3m5, 6, 11, 24, 26 | G3m24* |
| IGHG3*17 | G3m10, 11, 13, 15, 27 | G3m15* |
| IGHG3*18, IGHG3*19 | G3m10, 11, 13, 15, 16, 27 | G3m16* |
| IGHG3*14, IGHG3*15, IGHG3*16 | G3m21, 26, 27, 28 | G3m21* |

FIG. 2 presents the 32 peptides, also showing the enzymatic cleavage sites as well as the amino acids before and after the enzymatic cleavages. FIG. 2 also lists the corresponding masses of these peptides, determined for measurement with MALDI-MS and with ESI-MS. Table 6 summarizes the characteristics of the discriminatory peptides. Twenty-three (23) of the peptides are discriminatory of one single G3m allele. Nine of the peptides are even discriminatory for a single IGHG3 allele: the peptide of SEQ ID NO: 6 (G3 m5*), which is discriminatory for the IGHG3*09 allele; the peptides of SEQ ID NOs: 12, 18, 22, 26 and 30 (G3 m24*) which are discriminatory for the IGHG3*03 allele, and the peptides of SEQ ID NOs: 23, 27 and 31 (Gm6*) which are discriminatory for the IGHG3*13 allele. Each of the peptides of SEQ ID NO: 21 and of SEQ ID NO: 25 (see lines 21* and 21 and lines 25* and 25**** in Table 6) corresponds to two different G3m alleles: G3 m5* and G3 m21*. In those cases, the detection of another peptide should be required for an unambiguous G3m assignment, e.g. detection of the peptide of SEQ ID NO: 16 for G3 m5* and detection of the peptide of SEQ ID NO: 19 for G3 m21*, in the absence of serological data.

TABLE 6

Characteristics of the 32 proteotypic peptides for *Homo sapiens* G3m and IGHG3 alleles.

| Proteotypic Peptides (SEQ ID NO:) | Positions in CH domain [a] | Allotype and other polymorphic amino acids [b] | IGHG3 Alleles from IMGT/GENE-DB [c] | G3m Alleles simplified form [b] |
|---|---|---|---|---|
| CH2 domain | | | | |
| 1 | 79-85 | P82 (nG3m21), W83 (G3m16), Y84.3 | IGHG3*18, *19 | G3m16* |
| 2 | 79-85 | P82 (nG3m21), R83, Y84.3 | IGHG3*01, *02 [d], *04, *05, *06, *07, *09, *10 | G3m5* |
| | | | IGHG3*03 | G3m24* |
| | | | IGHG3*08 | Unusual [e] |
| | | | IGHG3*13 | G3m6* |
| | | | IGHG3*17 | G3m15* |
| | | | IGHG3*18, *19 | |
| 3 | 81-85 | L82 (G3m21), R83, Y84.3 | IGHG3*14, *15, *16 | G3m21* |
| 4 | 43-85 | P82, (nG3m21), W83 (G3m16), Y84.3 | IGHG3*18, *19 | G3m16* |
| 5 | 83-95 | R83, Y84.3, L92 | IGHG3*01, *02 [d], *04, *05, *06, *07, *10 | G3m5* |
| | | | IGHG3*03 | G3m24* |
| | | | IGHG3*08 | Unusual [e] |
| | | | IGHG3*13 | G3m6* |
| | | | IGHG3*17 | G3m15* |
| | | | IGHG3*14, *15, *16 | G3m21* |
| 6 | 83-95 | R83, Y84.3, V92 | IGHG3*09 | G3m5* |
| 7 | 79-95 | P82, W83 (G3m16), Y84.3, L92 | IGHG3*18, *19 | G3m16* |
| CH3 domain | | | | |
| 8 | 26-80 | V39, S44 (G3m11), K79 | IGHG3*06, *07 | G3m5* |
| | | | IGHG3*13 | G3m6* |
| 9 | 26-80 | M39 (G3m15 [g]), S44 (G3m11), K79 | IGHG3*17 | G3m15* |
| | | | IGHG3*18, *19 | G3m16* |

TABLE 6-continued

Characteristics of the 32 proteotypic peptides for *Homo sapiens* G3m and IGHG3 alleles.

| Proteotypic Peptides (SEQ ID NO:) | Positions in CH domain [a] | Allotype and other polymorphic amino acids [b] | IGHG3 Alleles from IMGT/GENE-DB [c] | G3m Alleles simplified form [b] |
|---|---|---|---|---|
| 10 | 26-84.2 | V39, S44 (G3m11), N79, M84 | IGHG3*01, *04, *05, *09, *10, *11 [f], *12 [c] | G3m5* |
| 12 | 26-84.2 | V39, S44 (G3m11), N79, V84 | IGHG3*03 | G3m24* |
| 13 | 26-84.2 | V39, N44 (nG3m11), N79, M84 | IGHG3*08<br>IGHG3*14, *16 | Unusual [e]<br>G3m21* |
| 14 | 33-80 | V39, S44 (G3m11), K79 | IGHG3*06, *07<br>IGHG3*13 | G3m5*<br>G3m6* |
| 15 | 33-80 | M39 (G3m15 [g]), S44 (G3m11), K79 | IGHG3*17<br>IGHG3*18, *19 | G3m15*<br>G3m16* |
| 16 | 33-84.2 | V39, S44 (G3m11), N79, M84 | IGHG3*01, *04, *05, *09, *10, *11 [f], *12 [c] | G3m5* |
| 18 | 33-84.2 | V39, S44 (G3m11), N79, V84 | IGHG3*03 | G3m24* |
| 19 | 33-84.2 | V39, N44 (nG3m11), N79, M84 | IGHG3*08<br>IGHG3*14, *16 | Unusual [e]<br>G3m21* |
| 20 | 93-120 | Q98 (G3m13 [h]), I101 (G3m27, G3m10 [i]), H115 + Y116 (nG3m5, G3m15 [j]) | IGHG3*17<br>IGHG3*18, *19 | G3m15*<br>G3m16* |
| 21* | 93-116 | Q98 (G3m13 [h]), I101 (G3m27, G3m10 [i]), R115 (G3m26) + F116 (G3m5, G3m14 [k]) | IGHG3*01, *04, *05, *06, *07, *09, *10, *11 [f], *12 [f]<br>IGHG3*08 | G3m5*<br>Unusual [e] |
| 21 | 93-116 | Q98, I101 (G3m27), R115 (G3m26) + Y116** (G3m28) | IGHG3*14, *15, *16 | G3m21* |
| 22 | 93-116 | E98 (G3m6 [l]), V101 (G3m24 [m]), R115 (G3m26) + F116 (G3m5) | IGHG3*03 | G3m*24 |
| 23 | 93-116 | E98 (G3m6 [l]), I101 (G3m27, G3m10 [i]), R115 (G3m26) + F116 (G3m5, G3m14 [k]) | IGHG3*13 | G3m6* |
| 24 | 95-120 | Q98 (G3m13 h), I101 (G3m27, G3m10 [i]), H115 + Y116 (nG3m5, G3m15 [j]) | IGHG3*17<br>IGHG3*18, *19 | G3m15*<br>G3m16* |
| 25* | 95-116 | Q98 (G3m13 [h]), I101 (G3m27, G3m10 [i]), R115 (G3m26) + F116** (G3m5, G3m14 [k]) | IGHG3*01, *04, *05, *06, *07, *09, *10, *11 [f], *12 [f]<br>IGHG3*08 | G3m5*<br>Unusual [e] |
| 25** | 95-116 | Q98, I101 (G3m27), R115 (G3m26) + Y116** (G3m28) | IGHG3*14, *15, *16 | G3m21* |
| 26 | 95-116 | E98 (G3m6 [l]), V101 (G3m24 [m]), R115 (G3m26) + F116 (G3m5) | IGHG3*03 | G3m24* |
| 27 | 95-116 | E98 (G3m6 [l]), I101 (G3m27, G3m10 [i]), R115 (G3m26) + F116 (G3m5, G3m14 [k]) | IGHG3*13 | G3m6* |
| 28 | 95-130 | Q98 (G3m13 [h]), I101 (G3m27, G3m10 [i]), H115 + Y116 (nG3m5, G3m15 [j]) | IGHG3*17<br>IGHG3*18, *19 | G3m15*<br>G3m16* |
| 29 | 95-120 | Q98 (G3m13 [h]), I101 (G3m27, G3m10 [i]), R115 (G3m26) + F116 (G3m5, G3m14 [k]) | IGHG3*01, *04, *05, *06, *07, *09, *10, *11 [f], *12 [f]<br>IGHG3*08 | G3m5*<br>Unusual [e] |
| 30 | 95-120 | E98 (G3m6 [l]), V101 (G3m24 [m]), R115 (G3m26) + F116 (G3m5) | IGHG3*03 | G3m*24 |
| 31 | 95-120 | E98 (G3m6 [l]), I101 (G3m27, G3m10 [i]), R115 (G3m26) + F116 (G3m5, G3m14 [k]) | IGHG3*13 | G3m6* |

TABLE 6-continued

Characteristics of the 32 proteotypic peptides for *Homo sapiens* G3m and IGHG3 alleles.

| Proteotypic Peptides (SEQ ID NO:) | Positions in CH domain [a] | Allotype and other polymorphic amino acids [b] | IGHG3 Alleles from IMGT/GENE-DB [c] | G3m Alleles simplified form [b] |
|---|---|---|---|---|
| 32 | 95-120 | Q98, I01 (G3m27), R115 (G3m26) + Y116 (G3m28) | IGHG3*14, *15, *16 | G3m21* |

[a] Lefranc et al., Dev. Comp. Immunol., 2005, 29: 185-203.
[b] Lefranc et al., Methods Mol. Biol., 2012, 882: 635-680.
[c] Giudicelli et al., Nucl. Acids Res., 2005, 33: D256-261.
[d] partial.
[e] Unusual G3m allele ([b]; Dard et al., Eur. J. Hum. Genet., 2001, 9: 765-772). This corresponds to the IGHG3*08 allele. Allotypes G3m10, G3m11 and G3m13 are not expressed owing to the presence of CH3 Asn N44, instead of the CH3 Ser S44 usually present in the other G3m5* alleles. [b]
[f] The IGHG3*11 and IGHG3*12 alleles differ by the number of hinge exons, 4 and 3, respectively (IMGT Repertoire, Gene table www.imgt.org). [b, c]
[g] Expression of the allotype G3m15 is dependent, in addition to CH3 Met M39, on the presence of CH3 His H115 and Tyr Y116. [b]
[h] Expression of the allotype G3m13 is dependent, in addition to CH3 Gln Q98, on the presence of CH3 Ser 44. [b]
[i] Expression of the allotype G3m10 is dependent, in addition to CH3 Ile I101, on the presence of CH3 Ser 44. [b]
[j] Expression of the allotype G3m15 is dependent, in addition to CH3 His H115 and Tyr Y116, on the presence of CH3 Met M39. [b]
[k] Expression of the allotype G3m14 is dependent, in addition to CH3 Arg R115 and Phe F116, on the presence of CH3 Met M84. [b]
[l] Expression of the allotype G3m6 is dependent, in addition to CH3 Glu E98, on the presence of CH3 Ser S44. [b]
[m] Expression of the allotype G3m24 is dependent, in addition to CH3 Val V101, on the presence of CH3 Ser S44. [b]
Amino acids in bold are implicated in the discrimination between IGHG3 alleles. "." : site of enzymatic cut.
Amino acids characteristic of the G3m allotypes and IGHG3 alleles are from Lefranc et al., Methods Mol. Biol., 2012, 882: 635-680. They are illustrated in the 'IMGT G3m allele butterfly' representation. Amino acid sequences are available in the IMGT Repertoire (www.imgt.org), IMGT/DomainDisplay and IMGT/GENE-DB. [b] Positions in the CH domains are according to the IMGT unique numbering for C domain. [a]
SEQ ID NO: 21*: K . SEQ ID NO: 21 . F
SEQ ID NO: 21**: K . SEQ ID NO: 21 . Y
SEQ ID NO: 25***: R . SEQ ID NO: 25 . F
SEQ ID NO: 25****: R . SEQ ID NO: 25 . Y

Figure 3:
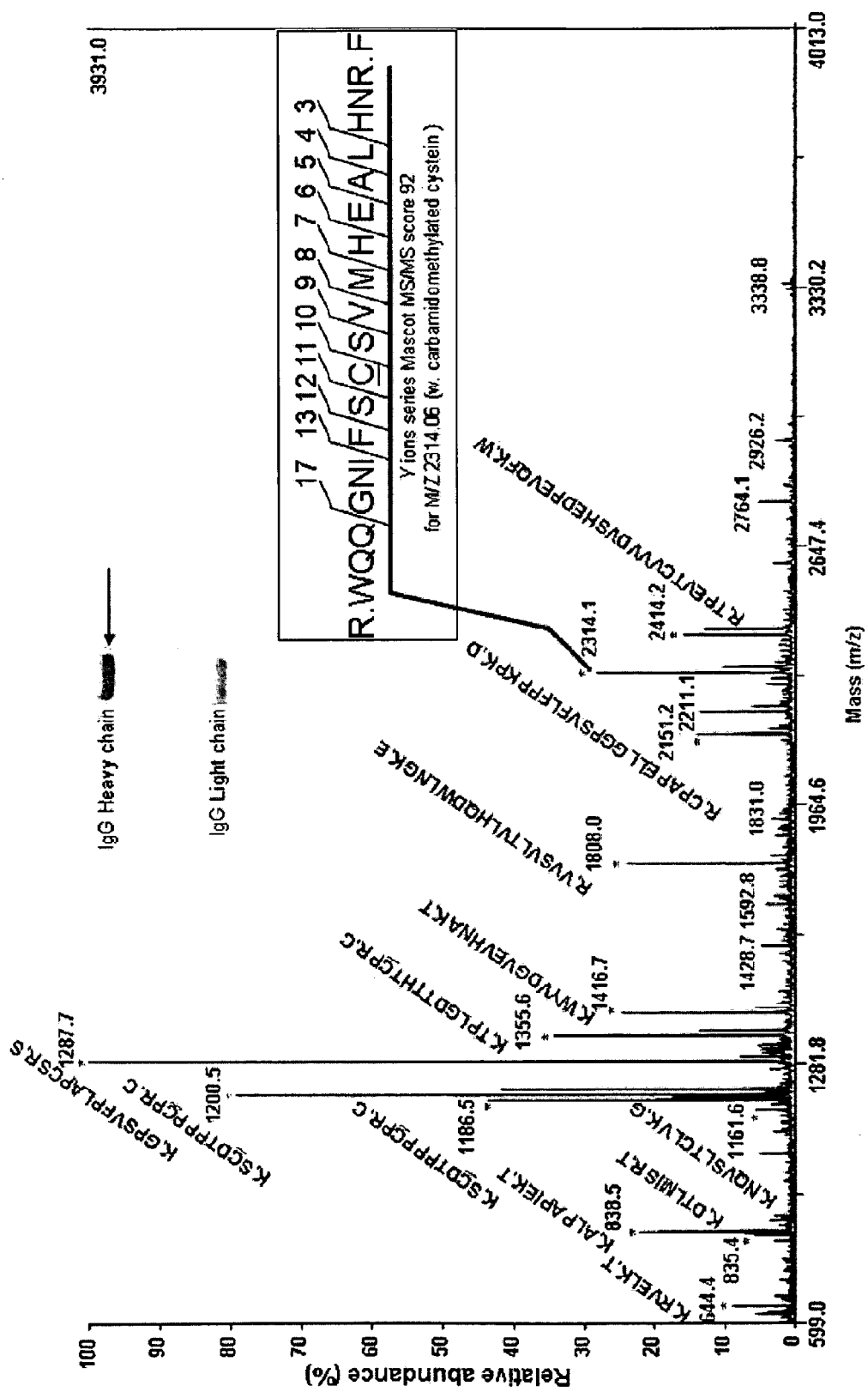
FIG. 3 is a MALDI-TOF spectrum of a heavy-chain tryptic digestion of purified IgG3s from a plasma sample from an individual of European origin. The tryptic peptides assigned corresponding to the masses labelled (*) are shown in red (green* for the propionamidated cysteines). The precursor selected with m/z of 2314.06 was submitted to CID fragmentation in MALDI in MS/MS mode. The fragmentation spectrum gives a Mascot result that unambiguously confirms the presence of the IGHG3 347-365 peptide: R.WQQGNIFSCSMHEALHNR.F whose mass makes it possible to discriminate the variations of amino acids.

4. MALDI-TOF/TOF Spectrum of the Digested Heavy Chain of Purified IgG3s from Plasma Sample Obtained from an Individual of French Origin As stated above, serological determination concluded that the French individual is homozygous for the allele G3 m5,10,11,13,14,26,27. The total IgG3s of a blood sample from this individual were isolated and the heavy chain of the IgG3s was submitted to enzymatic digestion in the presence of trypsin and AspN. MALDI-TOF/TOF analysis according to the invention made it possible to detect the peptide WQQGNIFSCSVMHEALHNR with m/z ratio=2314.06 (FIG. 3). In addition to the this peptide, another discriminating peptide of the allele G3 m5,10,11,13,14,26,27 was identified by ESI-LTQ-Orbitrap: DIAVEWESSGQPEN-NYNTTPP<u>M</u>L (with oxidation of the methionine) at m/z-870.05. The same spectra were obtained whether the sample was prepared from plasma obtained from freshly collected whole blood or after freezing and thawing.

Figure 4:
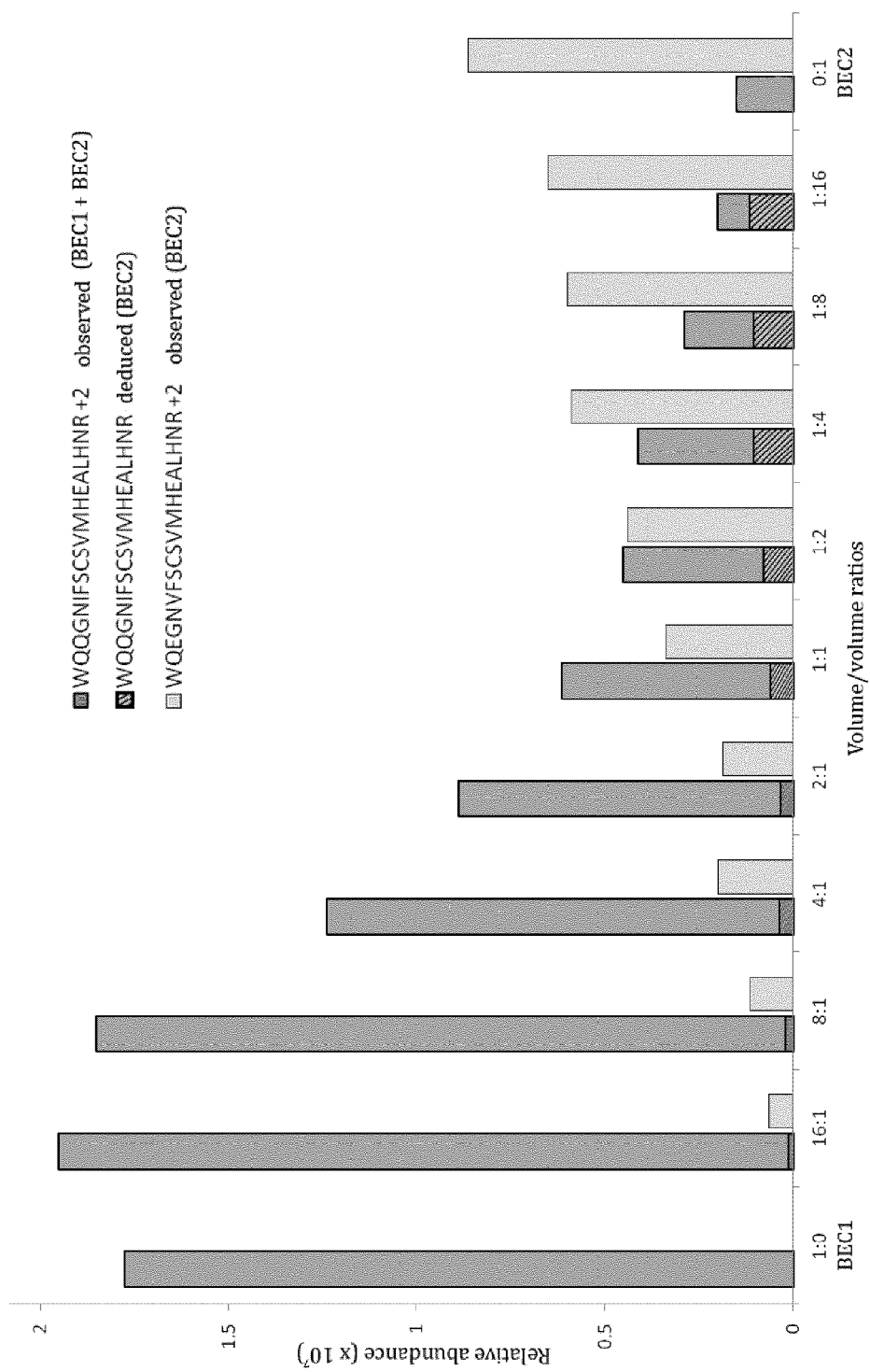
FIG. 4 is a graph showing the relative abundance of discriminating peptides of two G3m alleles as a function of different volume ratios of the two isoforms.

5. Sensitivity of the Method of Determining the G3m and IGHG3 Alleles by Mass Spectrometry The experiments were carried out on a series of controlled mixtures of plasma samples from two individuals in Benin who were found, by a serological method, to be homozygous for the alleles G3 m5,10,11,13,14,26,27 and G3 m5,6,11,24,26, respectively. The results of determination by mass spectrometry according to the invention show the presence of the peptide sequence WQQGNIFSCSVMHEALHNR for the first individual and of the peptide sequence WQEGN-VFSCSVMHEALHNR for the second individual. Mixing with volume/volume ratios as indicated in FIG. 4 was carried out before reduction, alkylation and enzymatic digestion.

There is a tendency for a gradual decrease of the discriminatory peptide 1 representative of the allele G3 m5,10,11,13,14,26,27 and conversely a gradual increase of the discriminatory peptide 2 representative of the allele G3 m5,6,11,24,26. In the 1:0 and 0:1 mixtures, the "missing" peptide was measured although it was not expected, which is explained by the fact that the background signal is measured by the software. Moreover, the resultant amount of peptides for these two volume ratios is lower than expected. In fact, this result is based on just one technical replicate taking into account a single form (+3) of the relevant peptides, the other two forms (+2, and M-oxidized 2+ and 3+) not having been considered. Nevertheless, the peptides were detected at least at the volume ratio of 1:16, indicating good sensitivity of the method of detection.

6. Application of the Proteomic Approach to Plasma Samples from a Mother and from her Child The experiments were carried out on the total IgG3s purified from plasma samples obtained from a Beninese mother (individual A170) and from her baby from birth to age 9 months (FIG. 5). As noted above, serological determination indicated that the mother was heterozygous (G3 m5,10,11,13,14,26,27/G3 m5,6,11,24,26,28) and that the child was homozygous for G3 m5,10,11,13,14,26,27. The results from determination by mass spectrometry according to the invention showed the presence of the peptide sequence WQQGNIFSCSVMHEALHNR in the mother and in the child.

The results obtained, presented in FIG. 5, showed an increase in the amount of the peptide WQQGNIFSCSVMHEALHNR between birth (sample CO) and age 3 months (sample M3) of the child. This increase can be explained by the appearance of the neo-synthesized IgG3s. A decrease in the amount of this peptide at age 6 months (sample M6) corresponds to the loss of maternal IgG3s transmitted during pregnancy, partially comprising this peptide. At 9 months (sample M9), only the IgG3s neo-synthesized by the child were observed.

7. Peptides Distinctive of G3m Alleles Observed by Mass Spectrometry

Mass spectrometry analysis of the plasma samples obtained from the individual of French origin, from the two Beninese children and from the Beninese mother and her child revealed three peptides, namely: DIAVEWESSGQPENNYNTTPPML (SEQ ID NO: 16), WQQGNIFSC$^c$SVMHEALHNR (SEQ ID NO: 25) and WQEGNVFSC$^c$SVMHEALHNR (SEQ ID NO: 26), all of which are included in the list of theoretical peptides presented in Table 4.

The IGHG3 alleles that they make it possible to distinguish correspond to the G3m alleles as follows (Lefranc et al., "Human Gm, Km and Am allotypes and their molecular characterization: a remarkable demonstration of polymorphism", In: Methods in Molecular Biology, Eds. B. Trait and F. Christiansen, in press):

DIAVEWESSGQPENNYNTTPPML (SEQ ID NO: 16) is distinctive of the alleles IGHG3*01, *04, *05, *09 to *13. WQQGNIFSC$^c$SVMHEALHNR (SEQ ID NO: 25) is distinctive of the alleles IGHG3*01, *02, *06 to *12, *14 to *16; and WQEGNVFSC$^c$SVMHEALHNR (SEQ ID NO: 26) is distinctive of the allele IGHG3*03, where IGHG3*01, *05, *06, *07, *09, *10, *11, *12 corresponds to the allele G3 m5,10,11,13,14,26,27; IGHG3*13 corresponds to the allele G3 m5,6,10,11,14,26,27; IGHG3*3 corresponds to the allele G3 m5,6,11,24,26 and IGHG3*14, *15, *16 corresponds to the allele G3 m21,26,27,28.

Limitations on the use of this method might be encountered in the rare cases when the mother and the child are either homozygous or heterozygous for the same G3m alleles. G3m polymorphism is not as extensive in certain groups of populations distributed throughout the world (Dugoujon et al., Am. J. Phys. Anthrop., 2004, 125: 175-192). In these cases, it will be necessary to resort to G1m polymorphism (4 IGHG1 alleles) to be sure of having the capacity to distinguish the IGHG alleles of the mother and of the child.

8. Selected Reaction Monitoring (SRM)

The WQEGNVFSCSVMHEALHNR peptide was expected in the mother's sample (CI) as well as in the samples corresponding the first months of life of her child (C0, M3, M6), but it was not visualized. The expected peptides DIAVEWESSGQPENNYNTTPPVL and DIAVEWESSGQPENNYNTTPPML were not observed in the Orbitrap. The detection threshold of these peptides seems to be too low in the sample.

Therefore, the optimized SRM strategy was used to monitor the WQEGNVFSCSVMHEALHNR and WQQGNIFSCSVMHEALHNR peptides with their corresponding AQUA peptides. The WQQGNIFSCSVMHEALHNR peptide was found and quantified in agreement with the Orbitrap data (FIG. 5B) but the detection of peptide WQEGNVFSCSVMHEALHNR was not possible in this particular case of mother-child pair samples. Two hypotheses may be proposed whereby i) BEM1 could be homozygous for the G3 m5* allele inversely to the results provided by the hemagglutination inhibition method or ii) the WQEGNVFSCSVMHEALHNR signal was undetected because it was lower than the signal/noise ratio.

In conclusion, both quantitative methods, either relative or absolute, provided satisfactory detection of the expected peptides from the two alleles whether in the artificial mixture or in the mother/neonate sera. Protein carbamidomethylation of cysteins was skipped in SRM experiments to avoid "multiple signals" of the peptide due to incomplete reaction.

---

What is claimed is:

1. An in vitro method for diagnosing, in a newborn, a vertically transmitted infectious disease caused by a pathogen, the method comprising steps of:
   identifying the pathogen;
   obtaining a blood sample from the newborn between the time of birth and the 9$^{th}$ month of the newborn's life,
   isolating the pathogen-specific IgG3s present in the blood sample obtained from the newborn, the blood sample comprising pathogen-specific IgG3s of the newborn and pathogen-specific IgG3s of maternal origin transmitted to the newborn during pregnancy;
   submitting the isolated pathogen-specific IgG3s to an enzymatic digestion in the presence of the endoproteinase AspN and of trypsin in order to obtain a mixture of proteotypic peptides of IgG3; and
   detecting, by mass spectrometry, among the mixture of proteotypic peptides of IgG3, the presence of at least one peptide distinctive of G3m and/or IGHG3 alleles in order to determine the G3m and IGHG3 alleles of the pathogen-specific IgG3s present in the blood sample obtained from the newborn, wherein the at least one peptide distinctive of G3m and/or IGHG3 alleles belongs to the group consisting of the peptides of SEQ ID NOs: 1 to 32, and any combination thereof;
   comparing the G3m and IGHG3 alleles of the pathogen-specific IgG3s present in the blood sample obtained from the newborn to the G3m and IGHG3 alleles of the IgG3s present in a blood sample obtained from the mother; and
   detecting, and optionally quantifying, the pathogen-specific IgG3s of the newborn.

2. The method according to claim 1, wherein mass spectrometry is performed using a tandem mass spectrometry technique, preferably MALDI-TOF/TOF, ESI-LTQ-Orbitrap or SRM MS/MS.

3. The method according to claim 1, wherein the blood sample obtained from the newborn is a plasma sample.

4. The method according to claim 1, wherein the G3m and IGHG3 alleles of the IgG3s present in the blood sample obtained from the mother are determined using an immunohaematologic technique, preferably a technique of haemagglutination inhibition.

5. The method according to claim 1, wherein the step of isolating the IgG3s or pathogen-specific IgG3s present in the blood sample obtained from the newborn comprises performing an affinity chromatography using a Protein A column and/or a Protein G column.

6. The method according to claim 1, wherein the vertically transmitted infectious disease is a viral infection, a bacterial infection or a parasitic infection, preferably selected from the group consisting of malaria caused by the pathogen *Plasmodium falciparum*, Chagas disease caused by the pathogen *Trypanosoma cruzi* and toxoplasmosis caused by the pathogen *Toxoplasma gondii*.

* * * * *